US008551966B2

(12) United States Patent
McGuigan et al.

(10) Patent No.: US 8,551,966 B2
(45) Date of Patent: Oct. 8, 2013

(54) CHEMICAL COMPOUNDS

(75) Inventors: Christopher McGuigan, Whitchurch (GB); Joachim J. Bugert, Penarth (GB); Arwyn T. Jones, Cardiff (GB); Ranjith Pathirana, Matara (LK); Laura E. Farleigh, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 144 days.

(21) Appl. No.: 13/193,343

(22) Filed: Jul. 28, 2011

(65) Prior Publication Data

US 2013/0012468 A1 Jan. 10, 2013

(30) Foreign Application Priority Data

Jul. 8, 2011 (GB) .................................. 1111779.3

(51) Int. Cl.
*A01N 43/04* (2006.01)
*A61K 31/70* (2006.01)
*C07H 19/22* (2006.01)
*C07H 19/16* (2006.01)

(52) U.S. Cl.
USPC .......................... 514/43; 536/27.14; 536/27.2

(58) Field of Classification Search
None
See application file for complete search history.

(56) References Cited

U.S. PATENT DOCUMENTS

| | | | | |
|---|---|---|---|---|
| 4,056,674 A | * | 11/1977 | Robins et al. ............... | 536/26.11 |
| 7,019,135 B2 | * | 3/2006 | McGuigan et al. ........... | 544/280 |
| 2007/0275910 A1 | | 11/2007 | McGuigan et al. | |

FOREIGN PATENT DOCUMENTS

| | | |
|---|---|---|
| WO | WO 98/49177 | 11/1998 |
| WO | WO 99/06422 | 2/1999 |
| WO | WO 01/83501 | 11/2001 |
| WO | WO 01/85749 | 11/2001 |
| WO | WO 2004/080466 | 9/2004 |
| WO | WO 2004/096813 | 11/2004 |
| WO | WO 2008/082440 | 7/2008 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Bidet et al., "Non-nucleoside structures retain full anti-HCMV potency of the dideoxy furanopyrimidine family", Antiviral Chemistry & Chemotherapy, vol. 15:329-332 (2004).
Li et al., "Synthesis of fluorescent nucleoside analogs as probes for 2'-deoxyribonucleoside kinases", Bioorganic & Medicinal Chemistry Letters, vol. 20:841-843 (2010).
Liu et al., "Directed evolution of an orthogonal nucleoside analog kinase via fluorescence-activated cell sorting", Nucleic Acids Research, vol. 37(13):4472-4481 (2009).
International Search Report and Written Opinion for application No. PCT/GB2012/051598, dated Aug. 30, 2012, by Claus Herz.
Berg et al., "Biochemistry" (Sixth Edition) published by W.H. Freeman and Company (2002) pp. 27, 303-310 and 322.
Blasco et al., "Extracellular vaccinia virus formation and cell-to-cell virus transmission are prevented by deletion of the gene encoding the 37,000-dalton outer envelope protein", Journal of Virology vol. 65:5910-5920 (1991).
Davison et al., "Structure of vaccinia virus early promoters", J. Mol. Boil. vol. 210(4):749-769 (1989).
Davison et al., "Structure of vaccinia virus late promoters", J. Mol. Biol. vol. 210(4):771-784 (1989).
Declaration of Joachim Jakob Bugert including Exhibits JJB1, JJB2, JJB3, dated Oct. 13, 2011 (87 pages).
McGuigan et al., "Discovery of a new family of inhibitors of human cytomegalovirus (HCMV) based upon lipophilic alkyl furano pyrimidine dideoxy nucleosides: action via a novel non-nucleosidic mechanism", J. Med. Chem. vol. 47:1847-1851 (2004).
Search Report for Application No. GB1111779.3, dated Oct. 19, 2011.

* cited by examiner

*Primary Examiner* — Traviss C McIntosh, III
(74) *Attorney, Agent, or Firm* — Fish & Richardson P.C.

(57) ABSTRACT

3-(2',3'-dideoxy-ribo-β-L-furanosyl)[2,3-d]pyrimidin-2 (3H)-one derivatives comprising 6-substitutents on the base moiety are shown to have anti-viral properties, particularly with respect to vaccinia and measles. The compounds have unnatural L ribose stereochemistry.

19 Claims, No Drawings

CHEMICAL COMPOUNDS

The present invention relates to chemical compounds suitable for use as anti-viral agent.

WO 01/85749 A1 relates to nucleoside analogues and their therapeutic use in the treatment of cytomegalo virus (CMV) and discloses the specific compounds: 3-[2′,3′-dideoxy-ribo-β-D-furanosyl]-6-R-2,3,-dihydro furo[2,3-d]pyrimidin-2-one, where R is -n-hexyl, -n-octyl, -n-nonyl, -[9-butyloxynonyl], -[9-(4-chlorobutoxy)nonyl], -n-decyl, -n-undecyl, -n-dodecyl or -n-tetradecyl. Each compound, as indicated by its name having regard to its furanosyl moiety, is in the D form. As set out in e.g. "Biochemistry" by Jeremy M. Berg, John L. Tymoczko and Lubert Stryer (Sixth Edition) published by W. H. Freeman and Company (2002) at Chapter 11, in a non-cyclised monosaccharide the D connotation refers to the absolute configuration of the asymmetric carbon atom farthest from the aldehyde group. Ribose has five C atoms, numbered C1 to C5, with C1 comprising the end aldehyde group and C4 comprising the asymmetric carbon atom farthest from the aldehyde group. In cyclised ribose, the 0 of the OH at the C4 atom bonds with the carbonyl C1 atom to provide a five membered ring comprising four C atoms and one O atom. The absolute configuration at C4 in open chain D-ribose thus determines the stereospecificity of cyclised ribo-D-furanosyl.

An additional asymmetric C centre is present when ribose is in its cyclic form. The C1 carbonyl atom in the open chain form of ribose becomes an asymmetric centre in the ring form. Where the OH moiety on the C1 atom in the cyclised form, or the base moiety attached to the C1 atom in a nucleoside, is on the same side of the furanosyl ring group as the $C5H_2OH$ group on the C4 atom, the cyclised ribose is called β-ribose. Each of the nucleoside compounds specifically mentioned above with respect to WO 01/85749 A1 is a β-ribose. Compounds where the OH or base moiety on the C1 atom is on the opposite side of the ring furanosyl group to the $C5H_2OH$ on the C4 atom are termed α-ribose.

In the ribo-β-D-furanosyl moiety in each of the above mentioned compounds specifically disclosed in WO 01/85749, the asymmetric centre at C4 is an S stereoisomer and the asymmetric centre at C1 is an R stereoisomer.

Reference is made to Berg, Tymoczko and Stryer, as above, at page 27 and at Chapter 11 having regard to the designation in the present application of an asymmetric C atom as being an S or R stereoisomer.

It is an object of the present invention to provide compounds having improved potency for treating viral infections and methods for using such compounds.

According to a first aspect of the present invention, there is provided a compound according to Formula I: I

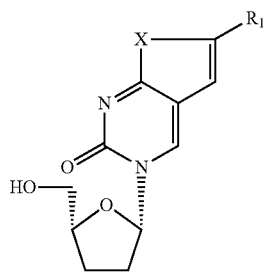

wherein:
$R_1$ is selected from the group consisting of:
  optionally substituted C5 to C20 alkyl;
  substituted C1 to C20 alkyl, wherein a substituent on said C1 to C20 alkyl is selected from the group consisting of $R_2O$— and $R_2S$— wherein $R_2$ is selected from the group consisting of optionally substituted C1 to C15 alkyl; and
  substituted aryl, wherein a substituent on said aryl is selected from the group consisting of optionally substituted C1 to C6 alkyl;
X is selected from the group consisting of O, S, NH, NMe, NEt and NiPr;
and pharmacologically acceptable salts, derivatives or prodrugs thereof.

As indicated by the configurational structure of Formula I, the compounds of the present invention are 2′,3′-dideoxy-ribo-β-L-furanosyl derivatives. The presently claimed compounds thus comprise, in combination, unnatural L ribose stereochemistry, having regard to the stereoisomerism at C4 of the ribose moiety, and 3-configuration, having regard to the stereoisomerism at C1 of the ribose moiety, the base attached at the ribose C1 position being on the same side of the furanosyl ring as the C5 moiety attached to the ribose C4 position. The compounds of the present invention are thus R stereoisomers at the asymmetric C atom comprising the C4 position in the cyclisised ribose moiety and S stereoisomers at the asymmetric C atom comprising the C1 position in the cyclisised ribose moiety. The presently claimed compounds thus differ from the compounds specifically disclosed in WO 01/85749 A1 with respect to their stereoisomeric centres at both the C1 and C4 positions in the cyclisised ribose moiety.

In addition to the essential ribo-β-L-furanosyl stereochemistry mentioned above with respect to the C1 and the C4 positions in the cyclicised ribose moiety, the presently claimed compounds are essentially 2′,3′-dideoxy compounds, i.e. they essentially have saturated and unsubstituted C2 and C3 atoms in the cyclicised ribose moiety.

The compounds of the present invention surprisingly show a significant potency having regard to viral infections, particularly vaccinia and/or measles infections.

Viral replication is a complex process that has conventionally proved difficult to combat with therapeutic agents. Different steps in the replication cycle of a virus, moreover, respond differently to different potential therapeutic agents. No expectation concerning the activity of the presently claimed β-L ribose compounds can thus be derived having regard to the disclosure of the β-D ribose compounds specifically mentioned above with reference to WO 01/85749 A1.

The efficacy of the present compounds is especially surprising as naturally occurring sugar moieties have D stereoisomerism. Traditionally, nucleoside derivatives were expected to act as nucleoside analogues and so necessarily require D-ribose chemistry to interfere with the D-ribose chemistry of DNA/RNA synthesis.

Where $R_1$ is optionally substituted C5 to C20 alkyl, it is suitably unsubstituted C5 to C20 alkyl, more suitably unsubstituted C6 to C12 alkyl and even more suitably C8 to C10 unsubstituted alkyl. Suitably $R_1$ is an acyclic, saturated, unbranched and unsubstituted alkyl. Suitably, $R_1$ is selected from the group consisting of n-hexyl-, n-heptyl-, n-octyl-, n-nonyl-, n-decyl- and n-dodecyl-, even more suitably $R_1$ is selected from the group consisting of n-octyl-, n-nonyl- and n-decyl-, and most suitably $R_1$ is n-nonyl-. Alternatively, where $R_1$ is an optionally substituted C5 to C20 alkyl, $R_1$ can be cyclic and/or unsaturated and/or branched and/or substituted with one to three substituents selected from the group consisting of F, Cl, Br and I. Where $R_1$ is an optionally substituted C5 to C20 alkyl and is unsaturated, the unsaturation can comprise one, two, three or more bonds selected independently from the group consisting of —C=C— and —C≡C— bonds. Whether acyclic or cyclic, saturated or unsaturated, branched or unbranched, substituted or unsubstituted, optionally substituted C5 to C20 alkyl $R_1$ is suitably C6 to C12. More suitably, $R_1$ is a C6 to C12 acyclic, saturated, unbranched and unsubstituted alkyl. Even more suitably, $R_1$ is C8 to C10 acyclic, saturated, unbranched and unsubstituted alkyl.

Where $R_1$ is a substituted C1 to C20 alkyl, it can comprise either a C1 to C20 alkylene (i.e. a saturated C chain moiety) or a C2 to C20 alkenylene (i.e. a C chain moiety containing one unsaturated C=C bond) bonded to an alkoxy moiety (i.e. $R_2O$—) or to a thioether moiety (i.e. $R_2S$—). A $R_2O$— moiety is the more suitable. Either of the said alkylene or alkenylene moieties can be branched or unbranched, acyclic or cyclic. Suitably $R_1$ comprises an acyclic and unbranched C1 to C20 alkylene moiety, more suitably an acyclic and unbranched C1 to C13 alkylene moiety. $R_2$ is suitably saturated, unbranched, acyclic and unsubstituted. More suitably, $R_2$ is selected from the group consisting of Me-, Et-, Pr-, Bu-, Pnt-, Hex-, Non-, Dec- and Trisdec, each of which is acyclic, saturated, unbranched and unsubstituted. Alternatively, $R_2$ can be unsaturated and/or can be branched and/or can be cyclic and/or can be substituted with one, two or three substituents independently selected from the group consisting of F, Cl, Br and I. Where $R_2$ is unsaturated, it can comprise one, two, three or more bonds independently selected from the group consisting of —C=C— and —C≡C— bonds. Where $R_1$ comprises a substituted C1 to C20 alkyl, it suitably comprises a single substituent. Where $R_1$ comprises a substituted C1 to C20 alkyl, it is suitably substituted at C1 alkylene or at the terminal position of a C2 to C20 alkylene or C2 to C20 alkenylene moiety. Suitably, where $R_1$ comprises a substituted C1 to C20 alkyl, it comprises a single substituent on a C1 alkylene or at the terminal position of a C2 to C20 alkylene or C2 to C20 alkenylene moiety and said single substituent is suitably $R_2O$. Suitably, where $R_1$ is substituted C1 to C20 alkyl, the total atomic backbone chain length of $R_1$, i.e. including $R_2$ and —O— or —S—, but excluding —H or any substituent on $R_2$, counting away from the base nucleoside moiety, is from 12 to 16, more suitably from 14 to 15. More suitably, $R_1$ comprises an unbranched, acyclic alkylene moiety having only a single substituent, wherein that single substituent is $R_2O$— present at the terminal position, if present, of the alkylene moiety and $R_2$ is acyclic, saturated, unbranched and unsubstituted alkyl, and the said total atomic backbone chain length of $R_1$ is from 12 to 16, even more suitably from 14 to 15. Most suitably where $R_1$ is substituted C1 to C20 alkyl, $R_1$ is n-pentyl-O—$C9H_{18}$—.

Where $R_1$ is substituted aryl, suitable substituents include C2 to C5 alkyl, more suitably unsubstituted C2 to C5 alkyl. Further suitable substituents include C4 and C5 alkyl, particularly unsubstituted C4 and C5 alkyl. Suitably, the alkyl substituents are acyclic, saturated, unbranched and unsubstituted. Where the alkyl substituents are themselves substituted, they can be substituted with one, two or three members independently selected from the group consisting of F, Cl, Br and I. Where the alkyl substitutents are unsaturated they can contain one, two or more bonds selected independently from the group consisting of —C=C— and —C≡C— bonds. Suitably, where $R_1$ is substituted aryl, it comprises only one substituent on its aryl moiety. Suitably $R_1$ is substituted phenyl, more suitably $R_1$ is substituted phenyl with only one substituent present, even more suitably $R_1$ is substituted phenyl with only one substituent present and with that one substituent present at the para position on phenyl. As an alternative to phenyl, the aryl moiety can be heterocyclic containing in total 4 to 12 ring atoms of which one, two or three are heteroatoms selected, independently, from O, N and S and/or the aryl moiety can comprise two or more fused rings. Where $R_1$ is substituted aryl, it suitably has a total atomic backbone chain length, i.e. including ring and alkyl C and ring heteroatoms, but excluding —H or substituents on alkyl and counting away from the base nucleoside moiety, of from 7 to 12, more suitably of from 8 to 9.

Suitably, X is O. Particularly suitable compounds have, in combination, X as O and $R_1$ as n-pentyl-O—$C_9H_{18}$—, n-octyl, n-nonyl or n-decyl. Especially suitable compounds have, in combination, X as O and $R_1$ as n-pentyl-$C_9H_{18}$— or n-octyl. Even more especially suitable, the compound of the present invention has, in combination, X as O and $R_1$ as n-pentyl-O—$C_9H_{18}$—.

Where X is NH, NMe, NEt or NiPr, X is suitably NMe. Where X is NH or NMe, and especially where X is NMe, $R_1$ is suitably substituted C1 to C20 alkyl, as defined above, and more suitably is n-pentyl-O—$C_9H_{18}$—. Even more suitably, a compound of the present invention has X as NMe, in combination, with $R_1$ as n-pentyl-O—$C9H_{18}$—

All possible combinations of X, as defined above, and $R_1$, as defined above, are specifically disclosed herein.

Pharmacologically acceptable salts, derivatives and pro-drugs of formula I include esters and salts of esters of formula I.

According to a further aspect of the present invention there is provided a compound of the present invention for use in a method of treatment, suitably in a method of prophylaxis or treatment of a viral infection, including vaccinia and/or measles.

According to a further aspect of the present invention there is provided a method of treatment or prophylaxis of a viral infection, including vaccinia and/or measles, comprising administering to patient in need thereof an effective dose of a compound of the present invention.

Compounds of the present invention are especially suitable for use in a method of prophylaxis or treatment of vaccinia where the compounds have X as 0 in combination with $R_1$ as unsubstituted C5 to C20 alkyl, especially unsubstituted C6 to C12 alkyl, even more especially unsubstituted C8 to C10 alkyl and even more especially C8 to C10 acyclic, saturated, unbranched and unsubstituted alkyl or have X as NMe in combination with $R_1$ as substituted C1 to C20 alkyl, as defined above, especially as PntO—$C_9H_{18}$—. Especially suitable methods of treatment or prophylaxis of the present invention are methods of treatment or prophylaxis of vaccinia where compounds of the present invention have combinations of X and $R_1$ as recited immediately above.

Compounds of the present invention are especially suitable for use in a method of prophylaxis or treatment of measles. Compounds of the present invention are especially suitable for use in a method of prophylaxis or treatment of measles where the compounds have X as O in combination with $R_1$ as substituted C1 to C20 alkyl, as defined above, more especially where $R_1$ comprises an unbranched, acyclic alkylene moiety having only one substituent, wherein that substituent is $R_2O$— present at the terminal position, if present, of the alkylene moiety and $R_2$ is acyclic, saturated, unbranched and unsubstituted alkyl, and the total atomic chain backbone chain length is from 12 to 16, even more especially from 14 to 15. Especially suitable methods of treatment or prophylaxis of the present invention are methods of treatment or prophylaxis of measles. Especially suitable methods of treatment or prophylaxis of the present invention are methods of treatment or prophylaxis of measles where the compounds of the present invention have combinations of X and $R_1$ as recited immediately.

According to a further aspect of the present invention there is provided a pharmaceutical composition comprising a compound of the present invention in combination with a pharmaceutically acceptable excipient.

According to a further aspect of the present invention there is provided a method of preparing a pharmaceutical composition comprising the step of combining a compound of the present invention with a pharmaceutically acceptable excipient.

According to a further aspect of the present invention there is provided a method of preparing a compound of the present invention comprising reacting a L-2',3'-dideoxy-5-halo-uridine with an alkyne of formula —C—$R_1$ in the presence of a catalyst, such as Pd, where $R_1$ is as defined above with respect to Formula I and uridine incorporates X as defined above with respect to formula I. Suitably the halo is iodo.

Medicaments comprising compounds of the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day, preferably in the range of 1 to 25 mg per kilogram body weight per day and most preferably in the range 5 to 10 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Embodiments of the present invention will now be described, by way of example only.

3-(2',3'-dideoxy-ribo-β-L-furanosyl)-6-hexylfuro[2,3-d]pyrimidin-2(3H)-one (Cf 3153)

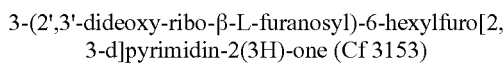

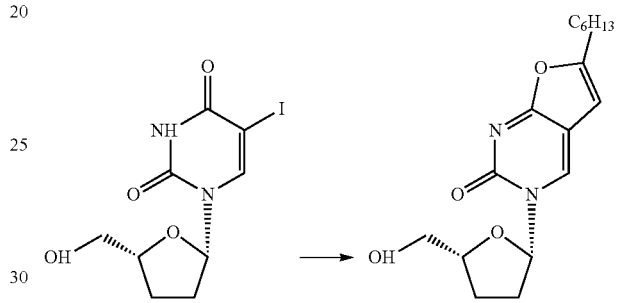

To a solution of L-2',3'-dideoxy-5-iodo-uridine (7) (0.30 g, 0.887 mmol) in DMF (5 ml) was added 1-Octyne (0.29 g, 0.4 ml, 2.66 mmol and 3 eq.), Tetrakis (triphenylphosphine) Pd(0) (0.103 g, 0.088 mmol and 0.1 eq.), CuI (0.034 g, 0.18 mmol, 0.2 eq.) and DIPEA (0.23 g, 1.77 mmol, 0.31 ml and 2 eq.). The mixture was stirred at room temperature for 16 h and further CuI (0.034 g, 0.18 mmol, 0.2 eq.) and TEA (5 ml) were added. The mixture was stirred at 80° C. for 8 h. The solvent was removed under high vacuum and the residue was purified by flash column chromatography (2% methanol in ethyl acetate) to obtain a pale brown oil which was found to be the uncyclized alkyne (130 mg, 0.374 mmol, 34%) This was dissolved in DMF (5 ml) and to this solution TEA (5 ml) and CuI (0.014 mg, 0.075 mmol, and 0.2 eq) were added. The resulting solution was heated at 80° for 8 h. Solvent was removed under high vacuum and the residue obtained was purified by preparative thin layer chromatography using 20% chloroform in ethyl acetate as the eluent.

Off white solid: 0.026 g (22%)

$^1$H-NMR (500 MHz, CDCl$_3$): 876 (1H, s, H-4), 6.20 (1H, m, H-1'), 6.15 (1H, s, H-5), 4.31 (1H, m, H-4'), 4.16 (1H, ddd $J_{5'-5'}$ 11.9 Hz, $J_{5'-4'}$ 4.2 Hz $J_{5'-OH}$ 2.9 Hz, H-5'), 3.89 (1H, ddd $J_{5'-5'}$ 11.9 Hz $J_{5'-4'}$ 3.0 Hz, H-5'), 2.69-2.54 (3H, m, CH$_2$+H-2'), 2.25-2.16 (1H, m, H-2'), 1.99-1.90 (2H, m, H-3'), 172 (2H, qn, J=7.1 Hz, CH$_2$), 1.41-1.22 (6H, m, 3×CH$_2$), 0.90 (3H, t J 6.3 Hz, CH$_3$)

$^{13}$C-NMR (125 MHz, CDCl$_3$): 171.74 (C7a), 159.47 (C6), 155.05 (C2), 135.98 (C4), 107.25 (C4a), 99.10 (C5), 89.00 (C1'), 82.93 (C4'), 62.81 (C5'), 33.79 (C2'), 31.43 (CH$_2$), 28.69 (CH$_2$), 28.25 (CH$_2$), 26.78 (C3'), 23.89 (CH$_2$), 22.50 (CH$_2$), 14.01 (CH$_3$) MS (m/z): 321 (100%), [M+H]$^+$, Accurate mass: C$_{17}$H$_{25}$N$_2$O$_4$ requires 321.1814, Observed 321.1824

HPLC: H$_2$O/MeOH, 100%-0 (0-25 mins), 0-100% (25-35 mins). Rt: 21.81 mins, 98.68%.

3-(2',3'-dideoxy-ribo-β-L-furanosyl)-6-septylfuro[2,3-d]pyrimidin-2(3H)-one (Cf 3174)

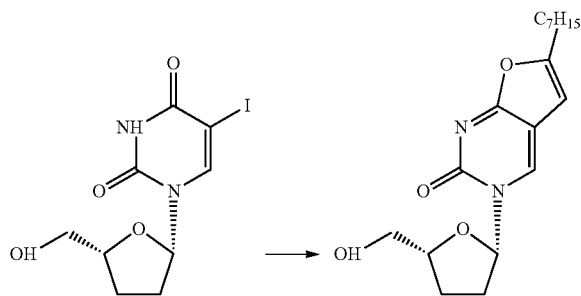

To a solution of L-2',3'-dideoxy-5-iodo-uridine (0.250 g, 0.739 mmol) in DMF (5 ml) were added 1-nonyne (0.275 g, 0.44 ml, 2.218 mmol, 3 eq.), tetrakis (triphenylphosphine) Pd(0) (0.085 g, 0.074 mmol, 0.1 eq.), CuI (0.028 g, 0.147 mmol, 0.2 eq) and DIPEA (0.191 g, 1.47 mmol, 0.26 ml, 2 eq). The mixture was stirred at room temperature for 16 h and further CuI (0.028 g, 0.147 mmol, 0.2 eq) and TEA (5 ml) were added. The mixture was stirred at 80° C. for 8 h. The solvent was removed under high vacuum and the residue obtained was purified by flash column chromatography (5% methanol in ethyl acetate) to obtain the title compound.

Off white solid: 0.128 g (53%)

$^1$H-NMR (500 MHz, CDCl$_3$): 8.84 (1H, s, H-4), 6.20 (1H, dd, J$_{1'-2'}$ 6.7 Hz, J$_{1'-2'}$ 2.5 Hz, H-1'), 6.16 (1H, s, H-5), 4.30 (1H, m, H-4'), 4.18 (1H, m, H-5'), 3.91 (1H, m, H-5'), 3.16 (1H, t J$_{5'-OH}$ 5.4 Hz, OH), 2.70-2.54 (3H, m, αCH$_2$+H-2'), 2.21 (1H, m, H-2'), 1.97 (2H, m, H-3'), 1.69 (2H, qn J 7.1 Hz, CH$_2$), 1.44-1.22 (8H, m, 4×CH$_2$), 0.90 (3H, t J 6.5 Hz, CH$_3$)

$^{13}$C-NMR (125 MHz, CDCl$_3$): 171.72 (C7a), 159.43 (C6), 155.06 (C2), 136.12 (C4), 107.25 (C4a), 99.15 (C5), 89.00 (C1'), 83.01 (C4'), 62.74 (C5'), 33.81 (C2'), 31.68 (CH$_2$), 28.98 (CH$_2$), 28.91 (CH$_2$), 28.25 (CH$_2$), 26.83 (C3'), 23.87 (CH$_2$), 22.59 (CH$_2$), 14.04 (CH$_3$)

MS (m/z): 335 (100%, [M+H]$^+$), 373 (9%, [M+K]$^+$), 398 (81%, [M+MeCNNa]$^+$), Accurate mass: C$_{18}$H$_{27}$N$_2$O$_4$ requires 335.1971, Observed 335.1958

HPLC: H$_2$O/MeOH, 100%-0 (0-15 mins), 10-90% (15-25 mins), 10%-90% (25-30 mins), 0-100% (30-40 mins). Rt: 17.91 mins, 98.81%.

3-(2',3'-dideoxy-ribo-β-L-furanosyl)-6-octylfuro[2,3-d]pyrimidin-2(3H)-one (Cf 3154)

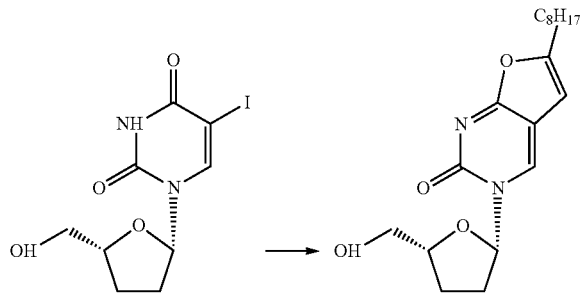

To a solution of L-2',3'-dideoxy-5-iodo-uridine (7) (0.25 g, 0.739 mmol) in DMF (5 ml) was added 1-decyne (0.31 g, 0.4 ml, 2.22 mmol and 3 eq.), Tetrakis (triphenylphosphine) Pd(0) (0.086 g, 0.073 mmol and 0.1 eq.), CuI (0.028 g, 0.147 mmol, 0.2 eq.) and DIPEA (0.191 g, 1.479 mmol, 0.26 ml and 2 eq.). The mixture was stirred at room temperature for 16 h and further CuI (0.028 g, 0.147 mmol, 0.2 eq.) and TEA (5 ml) were added. The mixture was stirred at 80° C. for 8 h. The solvent was removed under high vacuum and the residue was purified by flash column chromatography (2% methanol in ethyl acetate) to obtain a pale brown oil which on trituration with ethyl acetate gave the title compound.

Off white solid: 0.060 g (23%)

$^1$H-NMR (500 MHz, DMSO): 8.83 (1H, s, H-4), 6.42 (1H, s, 5.97 (1H, m, H-1'), 5.15 (1H, t J$_{5'-OH}$ 5.1 Hz, OH), 4.14 (1H, m, H-4'), 3.80 (1H, m, H-5'), 3.60 (1H, m, H-5'), 2.61 (2H, t J 7.2 Hz, αCH$_2$), 2.42 (1H, m, H-2'), 1.97 (1H, m, H-2'), 1.88-1.56 (2H, m, H-3'), 1.6 (2H, qn J 7.5 Hz, CH$_2$), 0.84 (3H, t J 6.7 Hz, CH$_3$)

$^{13}$C-NMR (125 MHz, DMSO): 170.99 (C7a), 158.01 (C6), 153.76 (C2), 137.00 (C4), 107.33 (C4a), 99.72 (C5), 88.02 (C1'), 83.00 (C4'), 61.33 (C5'), 33.03 (C2'), 31.16 (CH$_2$), 28.55 (CH$_2$), 28.50 (CH$_2$), 28.29 (CH$_2$), 27.29 (CH$_2$), 26.35 (C3'), 23.61 (CH$_2$), 22.00 (CH$_2$), 13.88 (CH$_3$)

MS (m/z): 349 (100%), [M+H]$^+$, Accurate mass: C$_{19}$H$_{29}$N$_2$O$_4$ requires 349.2127, Observed 349.2141

HPLC: H$_2$O/MeOH, 100%-0 (0-25 mins), 0-100% (25-30 mins). Rt: 26.04 mins, 97.72%

3-(2',3'-dideoxy-ribo+L-furanosyl)-6-nonylfuro[2,3-d]pyrimidin-2(3H)-one (Cf 3175)

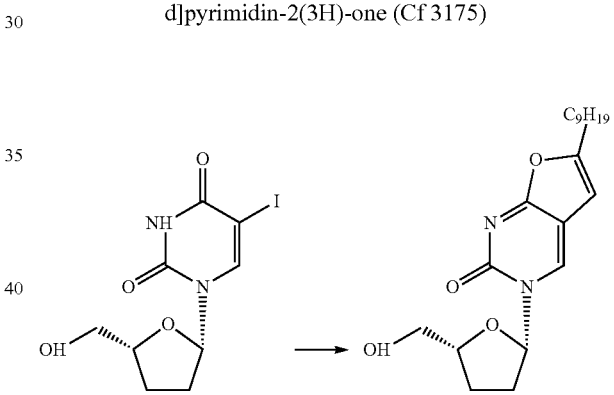

To a solution of L-2',3'-dideoxy-5-iodo-uridine (7) (0.300 g, 0.887 mmol) in DMF (5 ml) were added 1-undecyne (0.405 g, 2.66 mmol, 3 eq.), tetrakis (triphenylphosphine) Pd(0) (0.102 g, 0.089 mmol, 0.1 eq.), CuI (0.034 g, 0.177 mmol, 0.2 eq) and DIPEA (0.229 g, 1.77 mmol, 0.30 ml, 2 eq). The mixture was stirred at room temperature for 16 h and further CuI (0.034 g, 0.177 mmol, 0.2 eq) and TEA (5 ml) were added. The mixture was stirred at 80° C. for 8 h. The solvent was removed under high vacuum and the residue obtained was purified by flash column chromatography (60% ethyl acetate and 40% dichloromethane) to obtain the title compound.

Off white solid: 0.150 g (47%)

$^1$H-NMR (500 MHz, CDCl$_3$): 8.76 (1H, s, H-4), 6.20 (1H, dd, J$_{1'-2'}$ 6.8 Hz, J$_{1'-2'}$ 2.6 Hz, H-1'), 6.15 (1H, s, H-5), 4.31 (1H, m, H-4'), 4.17 (1H, m, H-5'), 3.91 (1H, m, H-5'), 2.83 (1H, t J$_{5'-OH}$ 5.5 Hz, OH), 2.70-2.55 (3H, m, αCH$_2$+H-2'), 2.24 (1H, m, 1.95 (2H, m, H-3'), 1.70 (2H, qn J 7.2 Hz, CH$_2$), 1.45-1.21 (12H, m, 6×CH$_2$), 0.90 (3H, t J 6.7 Hz, CH$_3$)

$^{13}$C-NMR (125 MHz, CDCl$_3$): 171.75 (C7a), 159.49 (C6), 155.02 (C2), 135.89 (C4), 107.22 (C4a), 99.07 (C5), 88.99 (C1'), 82.88 (C4'), 62.87 (C5'), 33.78 (C2'), 31.84 (CH$_2$), 29.45 (CH$_2$), 29.26 (CH$_2$), 29.04 (CH$_2$), 28.26 (CH$_2$), 26.83 (C3'), 23.91 (CH$_2$), 22.64 (CH$_2$), 14.08 (CH$_3$)

MS (m/z): 363 (53%), [M+H]$^+$, 426 (80%, [M+MeCNNa]$^+$), Accurate mass: C20H$_{31}$N$_2$O$_4$ requires 363.2284, Observed 363.2289

HPLC: H$_2$O/MeOH, 100%-0 (0-15 mins), 10-90% (15-25 mins), 10%-90% (25-30 mins), 0-100% (30-40 mins). Rt: 21.57 mins, 96.96%.

3-(2',3'-dideoxy-ribo-β-L-furanosyl)-6-decylfuro[2,3-d]pyrimidin-2(3H)-one (Cf 3155)

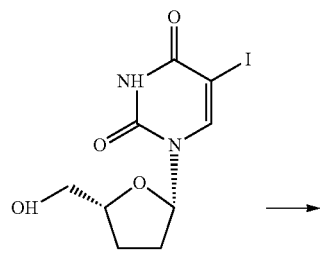

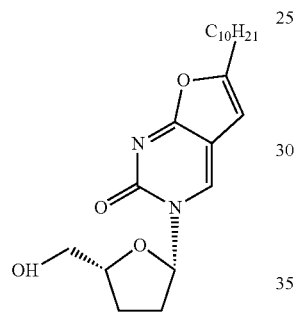

To a solution of L-2',3'-dideoxy-5-iodo-uridine (0.350 g, 1.04 mmol) in DMF (5 ml) were added 1-dodecyne (0.516 g, 0.7 ml, 3.11 mmol, 3 eq.), tetrakis (triphenylphosphine) Pd(0) (0.120 g, 0.104 mmol, 0.1 eq.), CuI (0.039 g, 0.207 mmol, 0.2 eq.) and DIPEA (0.267 g, 2.07 mmol, 0.36 ml, 2 eq.). The mixture was stirred at room temperature for 14 h and further CuI (0.039 g, 0.207 mmol, 0.2 eq) and TEA (5 ml) were added. The mixture was stirred at 80° C. for 6 h. The solvent was removed under high vacuum and the residue was purified by flash column chromatography (60% ethyl acetate and 40% dichloromethane) to obtain the title compound.

Off white solid: 0.100 g (33%)

$^1$H-NMR (500 MHz, CDCl$_3$): 8.75 (1H, s, H-4), 6.21 (1H, m, H-1'), 6.15 (1H, s, H-5), 4.32 (1H, m, H-4'), 4.17 (1H, m, H-5'), 3.90 (1H, m, H-5'), 2.86 (1H, t J$_{5'-OH}$ 5.4 Hz, OH), 2.68-2.57 (3H, m, αCH$_2$+H-2'), 2.21 (1H, m, H-2'), 1.96 (2H, m, H-3'), 1.72 (2H, qn J 7.0 Hz, CH$_2$), 1.44-1.21 (14H, m, 7×CH$_2$), 9.00 (3H, t J 6.4 Hz, CH$_3$)

$^{13}$C-NMR (125 MHz, CDCl$_3$): 171.75 (C7a), 159.49 (C6), 155.03 (C2), 135.90 (C4), 107.23 (C4a), 99.07 (C5), 88.99 (C1'), 82.88 (C4'), 62.86 (C5'), 33.78 (C2'), 31.87 (CH$_2$), 29.56 (CH$_2$), 29.50 (CH$_2$), 29.29 (CH$_2$), 29.27 (CH$_2$), 29.05 (CH$_2$), 28.26 (CH$_2$), 26.83 (C3"), 23.91 (CH$_2$), 22.66 (CH$_2$), 14.09 (CH$_3$)

MS (m/z): 377 (16%), [M+H]$^+$, 399 (6%, [M+Na]$^+$), 415 (8%, [M+K]$^+$), 440 (100%, [M+MeCNNa]$^+$), Accurate mass: C$_{21}$H$_{33}$N$_2$O$_4$ requires 377.2440, Observed 377.2426

HPLC: H$_2$O/MeOH, 100%-0 (0-30 mins), 0-100% (30-35 mins). Rt: 33.00 mins, 98.19%.

3-(2',3'-dideoxy-ribo-β-L-furanosyl)-6-dodecylfuro[2,3-d]-pyrimidin-2(3H)-one (Cf 3156)

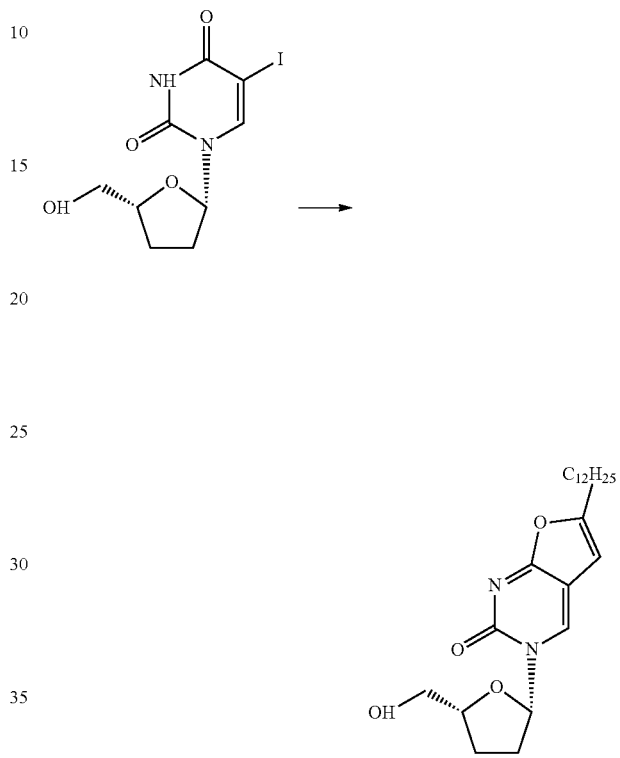

To a solution of L-2',3'-dideoxy-5-iodo-uridine (0.200 g, 0.591 mmol) in DMF (5 ml) were added 1-tetradecyne (0.345 g, 0.44 ml, 1.77 mmol, 3 eq.), tetrakis (triphenylphosphine) Pd(0) (0.068 g, 0.059 mmol, 0.1 eq.), CuI (0.023 g, 0.118 mmol, 0.2 eq) and DIPEA (0.153 g, 1.183 mmol, 0.20 ml, 2 eq). The mixture was stirred at room temperature for 16 h and further CuI (0.023 g, 0.118 mmol, 0.2 eq) and TEA (5 ml) were added. The mixture was stirred at 80° C. for 8 h. The solvent was removed under high vacuum and the residue obtained was purified by flash column chromatography (60% ethyl acetate and 40% dichloromethane) to obtain the title compound.

Off white solid: 0.100 g (42%)

$^1$H-NMR (500 MHz, CDCl$_3$): 8.77 (1H, s, H-4), 6.23 (1H, dd, J$_{1'-2'}$ 6.6 Hz, J$_{1'-2'}$ 2.5 Hz, H-1'), 6.16 (1H, s, H-5), 4.32 (1H, m, H-4'), 4.18 (1H, m, H-5'), 3.90 (1H, m, H-5'), 2.90 (1H, bs, OH), 2.67-2.56 (3H, m, αCH$_2$+H-2'), 2.21 (1H, m, H-2'), 1.94 (2H, m, H-3'), 1.69 (2H, qn J 7.5 Hz, CH$_2$), 1.43-1.20 (18H, m, 9×CH$_2$), 9.00 (3H, t J 6.5 Hz, CH$_3$)

$^{13}$C-NMR (125 MHz, CDCl$_3$): 171.74 (C7a), 159.48 (C6), 155.03 (C2), 135.95 (C4), 107.24 (C4a), 99.08 (C5), 88.99 (C1'), 82.91 (C4'), 62.83 (C5'), 33.79 (C2'), 31.90 (CH$_2$), 29.64 (CH$_2$), 29.61 (CH$_2$), 29.51 (CH$_2$), 29.33 (CH$_2$), 29.28 (CH$_2$), 29.06 (CH$_2$), 28.26 (CH$_2$), 26.84 (C3'), 23.90 (CH$_2$), 22.67 (CH$_2$), 14.10 (CH$_3$)

MS (m/z): 405 (100%), [M+H]$^+$, Accurate mass: C$_{23}$H$_{37}$N$_2$O$_4$ requires 405.2753, Observed 405.2739

HPLC: H₂O/MeOH, 100%-0 (0-15 mins), 10-90% (15-25 mins), 10%-90% (25-30 mins), 0-100% (30-40 mins). Rt: 28.99 mins, 98.26%.

3-(2',3'-dideoxy-ribo-β-L-furanosyl)-6-(4-n-butylphenyl)[2,3-d]pyrimidin-2(3H)-one (Cf 3176)

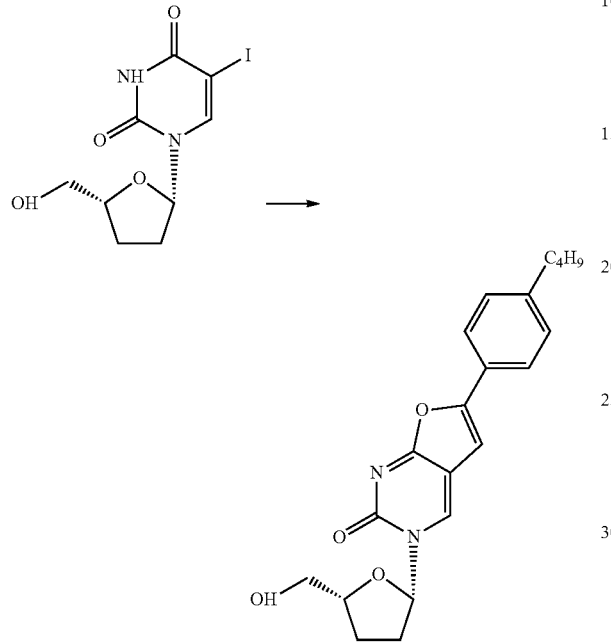

To a solution of L-2',3'-dideoxy-5-iodo-uridine (0.250 g, 0.739 mmol) in DMF (5 ml) was added 1-butyl-4-ethynylbenzene (0.351 g, 0.39 ml, 2.22 mmol and 3 eq.), tetrakis(triphenylphosphine) Pd(0) (0.085 g, 0.074 mmol and 0.1 eq.), CuI (0.028 g, 0.147 mmol, 0.2 eq.) and DIPEA (0.191 g, 1.47 mmol, 0.26 ml and 2 eq.). The mixture was stirred at room temperature for 15 h and further CuI (0.028 g, 0.147 mmol, 0.2 eq.) and TEA (5 ml) were added. The mixture was stirred at 80° C. for 8 h. The solvent was removed under high vacuum and the residue was purified by column chromatography (5% methanol in dichloromethane) to obtain the title compound.

Off white solid: 0.110 g (40%)

¹H-NMR (500 MHz, CDCl₃): 8.90 (1H, s, H-4), 7.63 (2H, d, $J_{a-b}$ 8.2 Hz, $H_a$), 7.22 (2H, d, $J_{b-a}$ 8.3 Hz, $H_b$), 6.71 (1H, s, H-5), 6.25 (1H, dd, $J_{1'-2'}$ 6.7 Hz, $J_{1'-2'}$ 2.3 Hz, H-1'), 4.32 (1H, m, H-4'), 4.2 (1H, m, H-5'), 3.92 (1H, m, H5'), 2.92 (1H, t $J_{5'-OH}$ 5.0 Hz, OH), 2.70-2.59 (3H, m, αCH₂+H-2'), 2.25 (1H, m, H-2'), 2.00 (2H, m, H-3'), 1.65 (2H, m, CH₂), 1.39 (2H, m, CH₂), 0.98 (3H, t J 6.6 Hz, CH₃)

¹³C-NMR (125 MHz, CDCl₃): 171.58 (C7a), 155.58 (C6), 155.00 (C2), 144.80 (para—C), 136.79 (C4), 128.96 (C—$H_a$), 125.98 (ipso—C), 124.82 (C—$H_b$), 107.81 (C4a), 97.22 (C5), 89.11 (C1'), 83.03 (C4'), 62.79 (C5'), 35.53 (CH₂), 33.85 (C2'), 33.36 (CH₂), 23.83 (C3'), 22.32 (CH₂), 13.91 (CH₃)

MS (m/z): 369 (44%), [M+H]⁺, 407 (70%, [M+K]⁺), 432 (50%, [M+MeCNNa]⁺), Accurate mass: C₂₁H₂₅N₂O₄ requires 369.1814, Observed 369.1830

HPLC: H₂O/MeOH, 100%-0 (0-35 mins), 0-100% (35-45 mins), Rt: 33.29 mins, 95.36%, 3-(2',3'-dideoxy-ribo-D-L-furanosyl)-6-(4-n-pentylphenyl) [2,3-d]pyrimidin-2(3H)-one (Cf 3177)

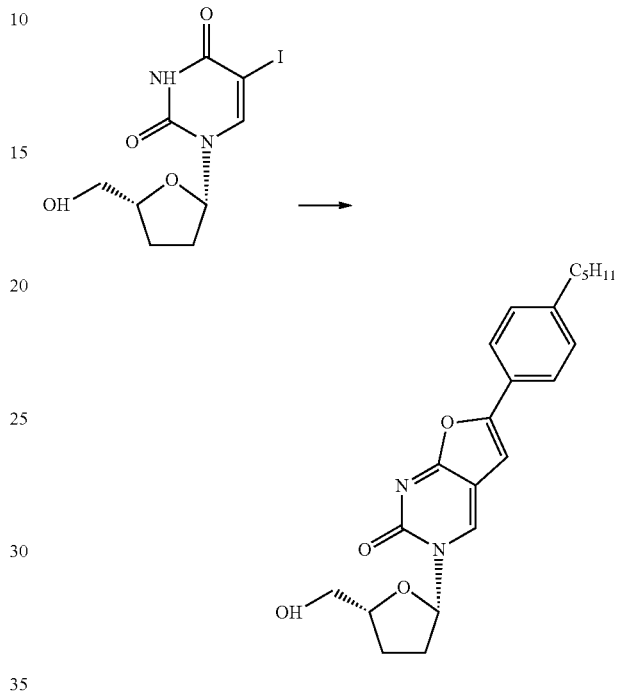

To a solution of L-2',3'-dideoxy-5-iodo-uridine (0.250 g, 0.739 mmol) in DMF (5 ml) was added 4-pentylphenylacetylene (0.382 g, 0.43 ml, 2.18 mmol and 3 eq.), tetrakis(triphenylphosphine) Pd(0) (0.085 g, 0.074 mmol and 0.1 eq.), CuI (0.028 g, 0.147 mmol, 0.2 eq.) and DIPEA (0.191 g, 1.47 mmol, 0.26 ml and 2 eq.). The mixture was stirred at room temperature for 15 h and further CuI (0.028 g, 0.147 mmol, 0.2 eq.) and TEA (5 ml) were added. The mixture was stirred at 80° C. for 8 h. The solvent was removed under high vacuum and the residue was purified by column chromatography (5% methanol in dichloromethane) to obtain the title compound.

Off white solid: 0.102 g (36%)

¹H-NMR (500 MHz, CDCl₃): 8.80 (1H, s, H-4), 7.68 (2H, d, $J_{a-b}$ 8.2 Hz, $H_a$), 7.26 (2H, d, $J_{b-a}$ 8.3 Hz, $H_b$), 6.70 (1H, s, H-5), 6.26 (1H, dd, $J_{1'-2'}$ 6.67 Hz, $J_{1'-2'}$ 2.26 Hz, H-1'), 4.35 (1H, m, H-4'), 4.20 (1H, m, H-5'), 3.90 (1H, m, H5'), 2.65 (3H, m, αCH₂+H-2'), 2.30-2.18 (2H, m, H-2'+OH), 1.95 (2H, m, H-3'), 1.61 (2H, m, CH₂), 1.42-1.29 (4H, m, 2×CH₂), 0.91 (3H, t J 6.5 Hz, CH₃)

¹³C-NMR (125 MHz, CDCl₃): 170.10 (C7a), 156.00 (C6), 155.50 (C2), 144.91 (para—C), 136.36 (C4), 128.99 (C—$H_a$), 126.00 (ipso—C), 124.87 (C—$H_b$), 125.98, 106.60 (C4a), 97.04 (C5), 89.10 (C1'), 82.76 (C4'), 63.04 (C5'), 35.83 (C2'), 33.78 (CH₂), 31.45 (CH₂), 30.92 (CH₂), 23.91 (C3'), 22.51 (CH₂), 13.99 (CH₃)

MS (m/z): 383 (14%), [M+H]⁺, 405 (3%, [M+Na]⁺), 421 (7%, [M+K]⁺), 446 (62%, [M+MeCNNa]⁺), Accurate mass: C₂₂H₂₇N₂O₄ requires 383.1971, Observed 383.1988

HPLC: H₂O/MeOH, 100%-0 (0-15 mins), 10-90% (15-25 mins), 10%-90% (25-30 mins), 0-100% (30-40 mins). Rt: 21.00 mins, 93.26%.

3-(2',3'-dideoxy-ribo-O-L-furanosyl)-6-ethyloxynonylfuro[2,3-d]pyrimidin 2(3H)-one (Cf 3210)

3-(2',3'-dideoxy-ribo-β-L-furanosyl)-6-propyloxynonylfuro[2,3-d]pyrimidin-2(3H)-one (Cf 3204)

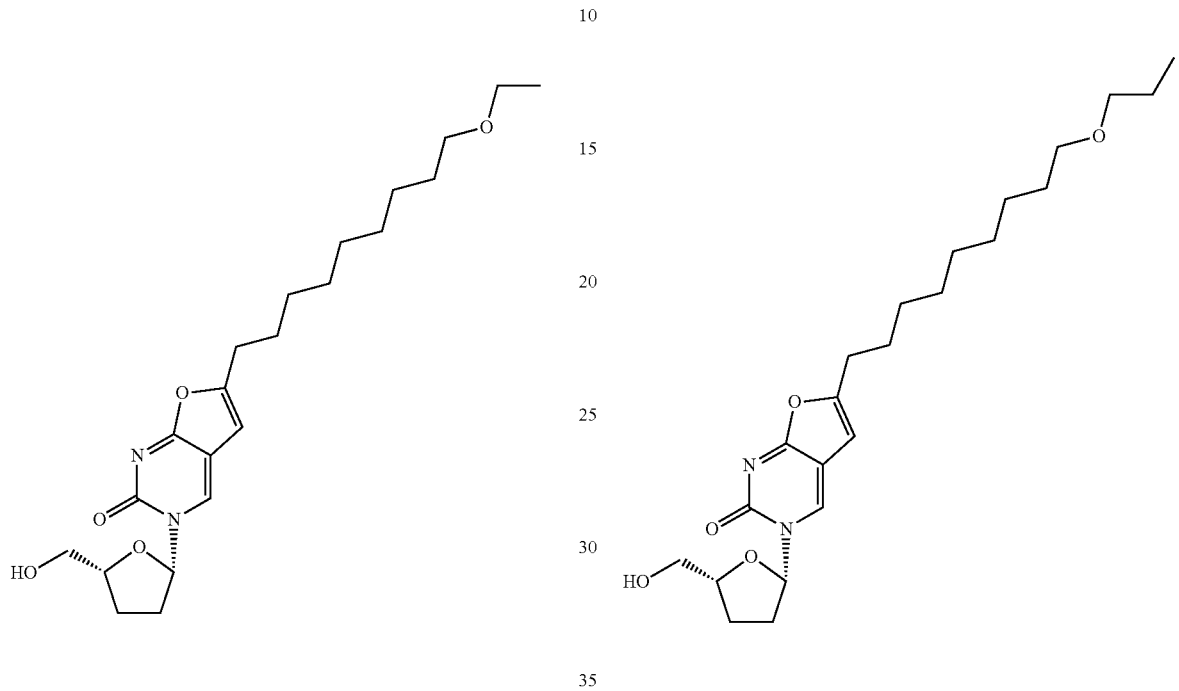

To a solution of L-2',3'-dideoxy-5-iodo-uridine (0.200 g, 0.592 mmol) in DMF (5 ml) was added 11-ethyloxy-1-undecyne (0.348 g, 1.775 mmol and 3 eq.), tetrakis (triphenylphosphine) Pd(0) (0.68 g, 0.059 mmol, 0.1 eq.), CuI (0.023 g, 0.118 mmol, 0.2 eq.) and DIPEA (0.153 g, 1.183 mmol, 0.21 ml, 2 eq.). The mixture was stirred at room temperature for 15 h and further CuI (0.023 g, 0.118 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) to obtain the title compound.

Off white solid: 0.102 g (42%)

$^1$H NMR (500 MHz, CDCl₃) δ 8.71 (s, 1H, H4), 6.21 (1H, dd, J, 6.7, 2.2 Hz, H1'), 6.13 (1H, s, H5), 4.33-4.28 (1H, m, H4'), 4.18-4.43 (1H, m, H5'a), 3.86 (1H, dt, J, 11.9, 3.8 Hz, H5'b), 3.49 (2H, q, J, 7.0 Hz, CH₃CH₂O), 3.42 (2H, t, J, 6.8 Hz, CH₂CH₂O), 2.65 (2H, t, J=7.4 Hz, αCH₂), 2.63-2.58 (1H, m, H2'a), 2.53 (1H, t, J, 4.7 Hz, OH), 2.26-2.19 (1H, m, H2'b), 1.99-1.90 (1H, m, H3'), 1.72-1.65 (2H, m, CH₂), 1.62-1.54 (2H, m, CH₂CH₂O), 1.40-1.25 (10H, m, 5×CH₂), 1.22 (3H, t, J, 7.0 Hz, CH₃).

$^{13}$C NMR (CDCl₃) δ 171.79 (C7a), 159.47 (C6), 154.98 (C2), 135.70 (C4), 107.15 (C4a), 99.02 (C5, 88.98 (C1'), 82.76 (C4'), 70.77 (CH₂CH₂O), 66.06 (CH₃CH₂O), 62.93 (C5') 33.76 (C2'), 29.69, 29.39, 29.35, 29.09, 28.88, 28.21, 26.73, 26.15 (8×CH₂), 23.91 (C3'), 15.24 (CH₃).

MS (m/z): 429 (100%, [M+Na]⁺), Accurate mass: C₂₂H₃₄N₂O₅Na requires 429.2365, Observed 429.2365

HPLC: H₂O/MeOH, 100%-0 (0-35 mins), 0-100% (35-45 mins), Rt: 33.25 mins, 96.18%.

To a solution of L-2',3'-dideoxy-5-iodo-uridine (0.250 g, 0.739 mmol) in DMF (5 ml) was added 11-propyloxy-1-undecyne (0.466 g, 2.218 mmol and 3 eq.), tetrakis (triphenylphosphine) Pd(0) (0.085 g, 0.074 mmol, 0.1 eq.), CuI (0.028 g, 0.147 mmol, 0.2 eq.) and DIPEA (0.191 g, 1.47 mmol, 0.26 ml, 2 eq). The mixture was stirred at room temperature for 15 h and further CuI (0.028 g, 0.147 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) to obtain the desired compound.

Off white solid: 0.105 g (34%)

$^1$H NMR (500 MHz, CDCl₃) δ 8.84 (1H, s, H4), 6.18 (1H, dd, J, 6.5, 2.0 Hz, H1'), 6.15 (1H, s, H5), 4.31-4.26 (1H, m, H4'), 4.18-4.10 (1H, m, H5'a), 3.87 (1H, dd, J, 12.0, 3.0 Hz, H5'b), 3.50 (1H, m, OH), 3.40 (2H, t, J=6.7 Hz, CH₂CH₂O), 3.37 (2H, t, J, 6.8 Hz, CH₂CH₂O), 2.63-2.54 (2H, m, αCH₂), 2.21-2.16 (1H, m, H2'b), 2.02-1.89 (1H, m, H3'), 169-1.50 (6H, m, 3×CH₂), 1.40-1.21 (10H, m, 5×CH₂), 0.92 (3H, t, J, 7.4 Hz, CH₃).

$^{13}$C NMR (CDCl₃) δ 171.68 (C7a), 159.33 (C6), 155.10 (C2), 136.32 (C4), 107.24 (C4a), 99.21 (C5), 89.00 (C1'), 83.10 (C4'), 72.55 (CH₂CH₂O), 70.88 (CH₃CH₂CH₂O'), 62.57 (C5') 33.82 (C2'), 29.74, 2×29.39 (double intensity), 29.13, 28.93, 28.20, 26.76, 26.13, (8×CH₂) 23.83 (C3') 22.91 (CH₂), 10.56 (CH₃)

MS (m/z): 443 (100%, [M+Na]⁺), Accurate mass: C₂₃H₃₆N₂O₅Na requires 443.2522, Observed 443.2539

HPLC: H₂O/MeOH, 100%-0 (0-35 mins), 0-100% (35-45 mins), Rt: 34.04 mins, 75.49%.

3-(2',3'-dideoxy-ribo-β-L-furanosyl)-6-butylox-ynonylfuro[2,3-d]pyrimidin-2(3H)-one (Cf 3207)

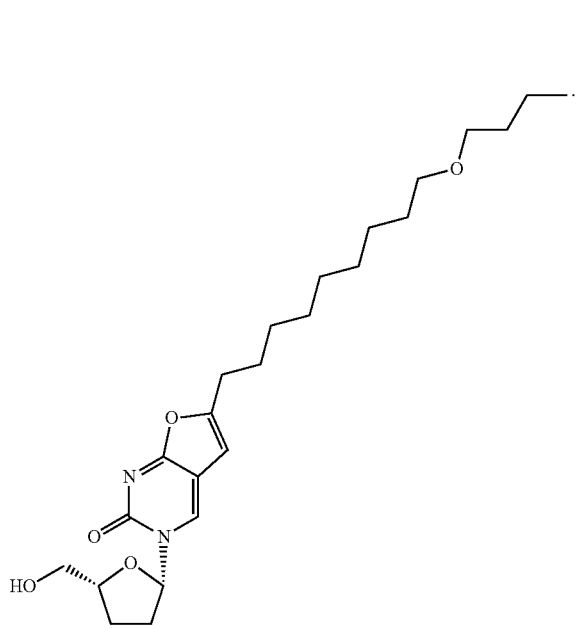 [SMILES: CCCCOCCCCCCCCCc1cc2cn([C@@H]3CC[C@H](CO)O3)c(=O)nc2o1]

To a solution of L-2',3'-dideoxy-5-iodo-uridine (0.250 g, 0.739 mmol) in DMF (5 ml) was added 11-butyloxy-1-undecyne (0.497 g, 2.217 mmol and 3 eq.), tetrakis (triphenylphosphine) Pd(0) (0.085 g, 0.074 mmol, 0.1 eq.), CuI (0.028 g, 0.147 mmol, 0.2 eq.) and DIPEA (0.191 g, 1.47 mmol, 0.26 ml, 2 eq). The mixture was stirred at room temperature for 15 h and further CuI (0.028 g, 0.147 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) to obtain the desired compound.

Off white solid: 0.090 g (28%)

$^1$H NMR (500 MHz, CDCl₃) δ 8.76 (1H, s, H4), 6.20 (1H, dd, J, 6.7, 2.4 Hz, H1'), 6.14 (1H, s, H5), 4.34-4.28 (1H, m, H4'), 4.20-4.12 (1H, m, H5'a), 3.88 (1H, dt, J, 11.9, 3.5 Hz, H5'b), 3.41 (4H, q, J, 6.1 Hz, CH₂OCH₂), 2.88 (1H, t, J=4.5 Hz, OH), 2.64 (2H, t, J, 7.3 Hz, αCH₂), 2.60 (1H, m, H2'a), 2.24-2.18 (1H, m, H2'b), 1.99-1.90 (1H, m, H3'), 1.71-1.61 (2H, m, βCH₂), 1.61-1.50 (4H, m, 2×CH₂), 1.44-1.24 (12H, m, 6×CH₂), 0.93 (3H, t, J, 7.4 Hz, CH₃)

$^{13}$C NMR (CDCl₃) δ 171.75 (C7a), 159.42 (C6), 155.02 (C2), 135.94 (C4), 107.18 (C4a), 99.09 (C5), 88.99 (C1'), 82.90 (C4'), 70.94 (CH₂CH₂O), 70.66 (OCH₂CH₂), 62.80 (C5'), 33.79 (C2'), 31.85, $\overline{29.76}$, 29.39, 29.$\overline{37}$, 29.12, 28.92, 28.21, 26.75, 26.14, (9×CH₂), 23.87 (C3'), 19.36 (CH₂), 13.93 (CH₃)

MS (m/z): 457 (100%, [M+Na]⁺), Accurate mass: C₂₄H₃₉N₂O₅ requires 435.2859, Observed 435.2839

HPLC: H₂O/MeOH, 100%-0 (0-35 mins), 0-100% (35-45 mins), Rt: 35.15 mins, 81.00%.

3-(2',3'-dideoxy-ribo-β-L-furanosyl)-6-pentylox-ynonylfuro[2,3-d]pyrimidin-2(3H)-one (Cf 3208)

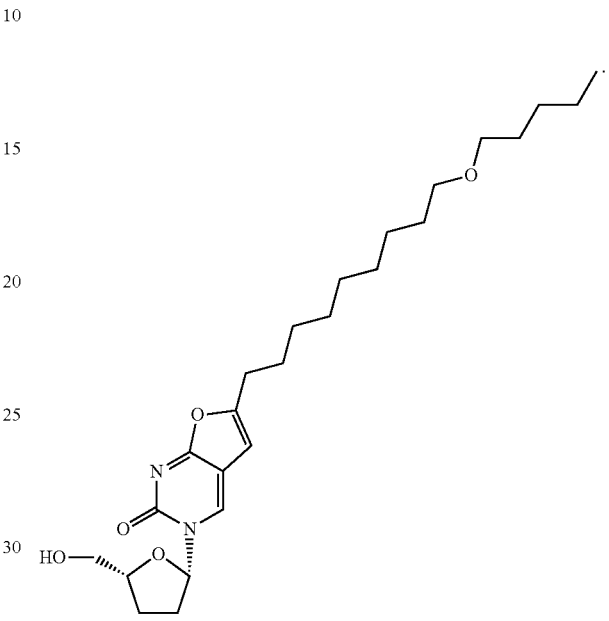

To a solution of L-2',3'-dideoxy-5-iodo-uridine (0.220 g, 0.650 mmol) in DMF (5 ml) was added 11-pentyloxy-1-undecyne (0.465 g, 1.952 mmol and 3 eq.), tetrakis (triphenylphosphine) Pd(0) (0.075 g, 0.065 mmol, 0.1 eq.), CuI (0.025 g, 0.130 mmol, 0.2 eq.) and DIPEA (0.168 g, 1.301 mmol, 0.23 ml, 2 eq). The mixture was stirred at room temperature for 15 h and further CuI (0.025 g, 0.130 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) to obtain the desired compound.

Off white solid: 0.102 g (35%)

$^1$H NMR (500 MHz, CDCl₃) δ 8.76 (1H, s, H4), 6.20 (1H, dd, J, 6.7, 2.5 Hz, H1'), 6.14 (1H, s, H5), 4.33-4.29 (1H, m, H4'), 4.18-4.13 (1H, m, H5'a), 3.88 (1H, dt, J, 12.0, 3.9 Hz, H5'b), 3.41 (4H, td, J, 6.7, 0.9 Hz, CH₂OCH₂), 2.90 (1H, bs, OH), 2.64 (2H, t, J, 7.5 Hz, αCH₂), 2.63-2.56 (1H, m, H2'a), 2.25-2.18 (1H, m, H2'b), 2.00-1.91 (2H, m, H3'), 1.72-1.63 (2H, m, βCH₂), 1.61-1.55 (4H, m, 2×CH₂), 1.35-1.28 (14H, m, 7×CH₂), 0.91 (3H, t, J, 6.9 Hz, CH₃)

$^{13}$C NMR (CDCl₃) δ 171.75 (C7a), 159.41 (C6), 155.01 (C2), 135.96 (C4), 107.18 (C4a), 99.09 (C5), 88.99 (C1'), 82.91 (C4'), 70.98 (CH₂CH₂O), 70.94 (OCH₂CH₂), 62.79 (C5'), 33.79 (C2'), 29.76, $\overline{29.45}$, 29.39, 29.$\overline{38}$, 29.12, 28.92, 28.36, 28.21, 26.75, 26.14, (10×CH₂), 23.87 (C3'), 22.54 (CH₂), 14.04 (CH₃)

MS (m/z): 449 (11%), [M+H]⁺, 471 (100%, [M+Na]⁺),

Accurate mass: C₂₅H₄₁N₂O₅ requires 449.3015, Observed 449.3033

HPLC: H₂O/MeOH, 100%-0 (0-35 mins), 0-100% (35-45 mins), Rt: 26.13 mins, 98.25%.

3-(2',3'-dideoxy-ribo-β-L-furanosyl)-6-hexyloxynonylfuro[2,3-d]pyrimidin-2(3H)-one (Cf 3209)

HPLC: H₂O/MeOH, 100%-0 (0-15 mins), 10-90% (15-25 mins), 10-90% (25-30 mins), 0-100% (30-40 mins), Rt: 26.91 mins, 87.56%.

3-(2',3'-dideoxy-ribo-β-L-furanosyl)-6-hexyloxyoctylfuro[2,3-d]pyrimidin-2(3H)-one (Cf 3230)

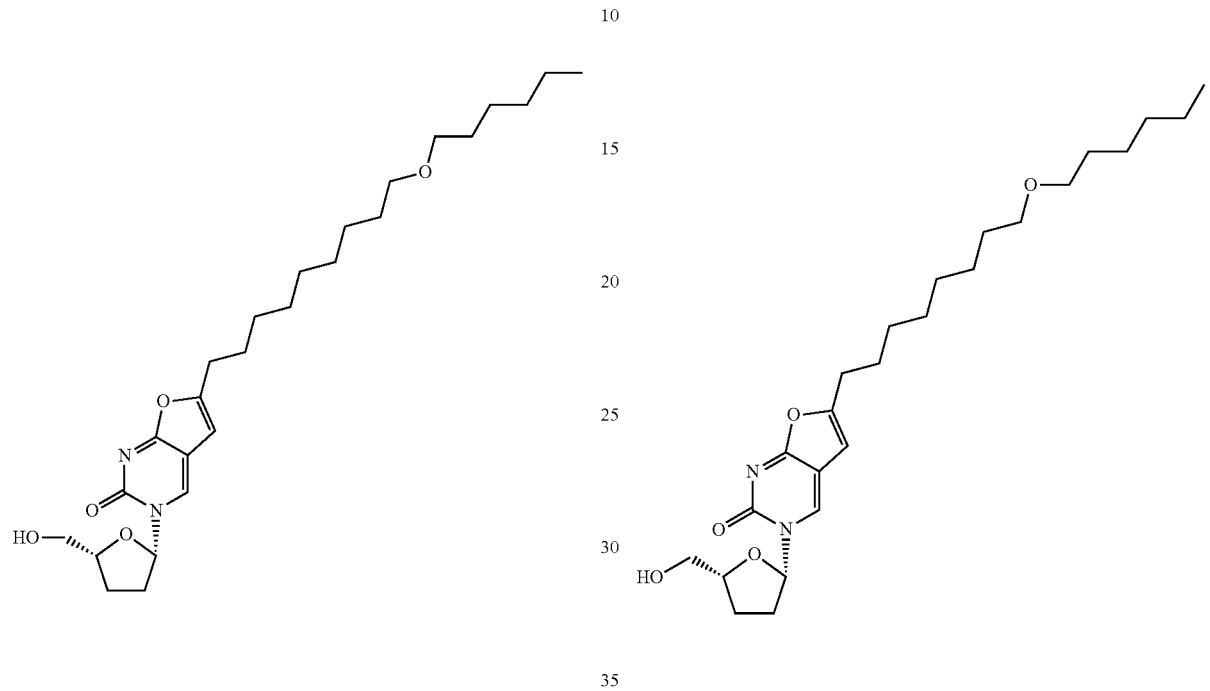

To a solution of L-2',3'-dideoxy-5-iodo-uridine (0.200 g, 0.592 mmol) in DMF (5 ml) was added 11-hexyloxy-1-undecyne (0.448 g, 1.775 mmol and 3 eq.), tetrakis (triphenylphosphine) Pd(0) (0.068 g, 0.059 mmol, 0.1 eq.), CuI (0.023 g, 0.118 mmol, 0.2 eq.) and DIPEA (0.53 g, 1.183 mmol, 0.21 ml, 2 eq). The mixture was stirred at room temperature for 15 h and further CuI (0.023 g, 0.118 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) to obtain the desired compound.

Off white solid: 0.120 g (44%)

$^1$H NMR (500 MHz, CDCl₃) δ 8.76 (1H, s, H4), 6.21 (1H, dd, J, 6.7, 2.3 Hz, H1'), 6.14 (1H, s, H5), 4.33-4.29 (1H, m, H4'), 4.19-4.13 (1H, m, H5'a), 3.87 (1H, dt, J, 12.0, 3.9 Hz, H5'b), 3.41 (4H, td, J, 6.7, 1.3 Hz, CH₂OCH₂), 2.87 (1H, t, J, 4.9 Hz, OH), 2.64 (2H, t, J, 7.3 Hz, αCH₂), 2.63-2.57 (1H, m, H2'a), 2.24-2.19 (1H, m, H2'b), 1.98-1.92 (2H, m, H3'), 1.71-1.65 (2H, m, 13 CH₂), 1.69-1.53 (4H, m, 2×CH₂), 1.38-1.26 (16H, m, 8×CH₂), 0.90 (3H, t, J, 6.9 Hz, CH₃)

$^{13}$C NMR (CDCl₃) δ 171.75 (C7a), 159.41 (C6), 155.01 (C2), 135.93 (C4), 107.17 (C4a), 99.08 (C5), 88.98 (C1'), 82.89 (C4'), 71.00 (CH₂CH₂O), 70.94 (OCH₂CH₂), 62.80 (C5'), 33.79 (C2'), 31.71, 29.76, 29.73, 29.39, 29.38, 29.12, 28.92, 28.21, 26.75, 26.15, 25.86 (11×CH₂), 23.87 (C3'), 22.62 (CH₂), 14.03 (CH₃).

MS (m/z): 463 (5%), [M+H]⁺, 485 (100%, [M+Na]⁺), 501 (8%, [M+K]⁺), Accurate mass: C₂₆H₄₃N₂O₅ requires 463.3172, Observed 463.3163

To a solution of L-2',3'-dideoxy-5-iodo-uridine (0.200 g, 0.592 mmol) in DMF (5 ml) were added 10-hexyloxy-1-decyne (0.352 g, 1.48 mmol, 2.5 eq.), tetrakis (triphenylphosphine) Pd(0) (0.068 g, 0.059 mmol, 0.1 eq.), CuI (0.023 g, 0.118 mmol, 0.2 eq.) and DIPEA (0.153 g, 1.183 mmol, 0.21 ml, 2 eq). The mixture was stirred at room temperature for 15 h and further CuI (0.023 g, 0.118 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) to obtain the desired compound.

Off white solid: 0.080 g (30%)

$^1$H NMR (500 MHz, CDCl₃) δ 8.73 (1H, s, H4), 6.21 (1H, dd, J, 6.1, 1.8 Hz, H1'), 6.13 (1H, s, 1-15), 4.34-4.27 (1H, m, H4'), 4.19-4.12 (1H, m, H5'a), 3.88 (1H, td, J, 7.6, 4.0 Hz, H5'b), 3.41 (4H, t, J, 6.1 Hz, CH₂OCH₂), 2.71 (1H, t, J, 4.7 Hz, OH), 2.67-2.56 Hz (3H, m, αCH₂+H2'a), 2.26-2.18 (1H, m, H2'b), 2.00-1.91 (2H, m, H3'), 1.77-1.64 (2H, m, βCH₂), 1.62-1.52 (4H, m, 2×CH₂), 1.42-1.23 (14H, m, 7×CH₂), 0.90 (3H, t, J, 6.8 Hz, CH₃)

$^{13}$C NMR (CDCl₃) δ 171.76 (C7a), 159.44 (C6), 154.99 (C2), 135.83 (C4), 107.17 (C4a), 99.05 (C5), 88.99 (C1'), 82.83 (C4'), 71.00 (CH₂CH₂O), 70.89 (OCH₂CH₂), 62.88 (C5'), 33.77 (C2'), 31.71, 29.73, 29.32, 2×29.19 (double intensity), 28.94, 28.23, 26.78, 26.14, 25.86 (10×CH₂), 23.90 (C3'), 22.62 (CH₂), 14.04 (CH₃)

MS (m/z): 449 (11%), [M+H]⁺, 471 (64%, [M+Na]⁺), 487 (100%, [M+K]⁺), Accurate mass: C₂₅H₄₁N₂O₅ requires 449.3015, Observed 449.3033

HPLC: H₂O/MeOH, 100%-0 (0-35 mins), 0-100% (35-45 mins), Rt: 38.17 mins, 85.45%.

3-(2',3'-dideoxy-ribo-β-L-furanosyl)-6-decyloxybutylfuro[2,3-d]pyrimidin-2(3H)-one (Cf 3231)

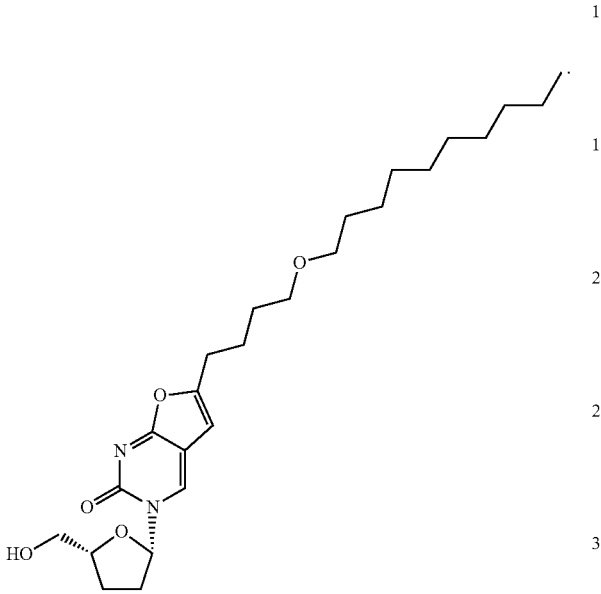

To a solution of L-2',3'-dideoxy-5-iodo-uridine (0.200 g, 0.592 mmol) in DMF (5 ml) were added 1-(Hex-5-ynyloxy) decane (0.352 g, 1.776 mmol, 3.0 eq), tetrakis (triphenylphosphine) Pd(0) (0.068 g, 0.059 mmol, 0.1 eq.), CuI (0.023 g, 0.118 mmol, 0.2 eq.) and DIPEA (0.153 g, 1.183 mmol, 0.21 ml, 2 eq). The mixture was stirred at room temperature for 15 h and further CuI (0.023 g, 0.118 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) to obtain the desired compound.

Off white solid: 0.070 g (26%)

¹H NMR (500 MHz, CDCl₃) δ 8.72 (1H, s, H4), 6.21 (1H, bd, J, 6.1 Hz, H1'), 6.14 (1H, s, H5), 4.34-4.28 (1H, m, H4'), 4.19-4.12 (1H, m, H5'a), 3.91-3.86 (1H, m, H5'b), 3.45 (2H, t, J, 6.3, 2.1 Hz, CH₂OCH₂), 3.41 (2H, t, J, 6.7, 2.1 Hz, CH₂OCH₂), 2.69 (2H, t, 7.4, αCH₂), 2.64-2.57 (2H, m, H2'a+OH), 2.23-2.19 (1H, m, 2'b), 1.98-1.92 (2H, m, H3'), 1.81-1.73 (2H, m, βCH₂), 1.69-1.62 (2H, m, CH₂), 1.60-1.54 (2H, m, CH₂), 1.35-1.24 (12H, m, 6×CH₂), 0.90 (3H, t, J, 6.5 Hz, CH₃).

¹³C NMR (CDCl₃) δ 171.75 (C7a), 159.11 (C6), 154.97 (C2), 135.87 (C4), 107.10 (C4a), 99.23 (C5), 89.00 (C1'), 82.81 (C4'), 71.15, 70.23 (CH₂OCH₂), 62.92 (C5'), 33.77 (C2'), 29.74, 29.60, 29.57, 29.49, 29.31, 29.12 (6×CH₂) 28.08 (a CH₂), 26.18 (CH₂), 23.90 (C3'), 23.68 (βCH₂), 22.67 (CH₂), 14.10 (CH₃).

MS (m/z): 449 (17%), [M+H]⁺, 471 (6%, [M+Na]⁺), 487 (4%, [M+K]⁺), 512 (100%, [M+MeCNNa]⁺), Accurate mass: C₂₅H₄₁N₂O₅ requires 449.3015, Observed 449.3028

HPLC: H₂O/MeOH, 100%-0 (0-15 mins), 10-90% (15-20 mins), 10-90% (20-25 mins), 0-100% (25-35 mins), Rt: 26.45 mins, 87.74%.

3-(2',3'-dideoxy-ribo-β-L-furanosyl)-6-tridecyloxymethylfuro[2,3-d]pyrimidin-2(3H)-one (Cf 3232)

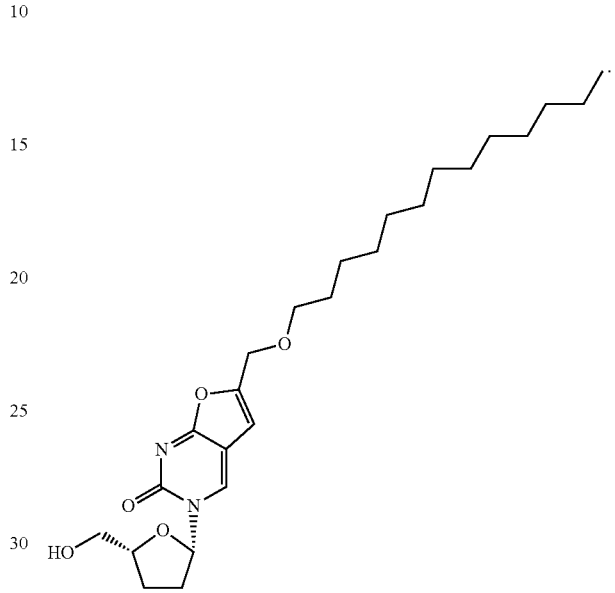

To a solution of L-2',3'-dideoxy-5-iodo-uridine (0.200 g, 0.592 mmol) in DMF (5 ml) were added 1-(Prop-2-ynyloxy) tridecane (0.352 g, 1.776 mmol, 3.0 eq), tetrakis (triphenylphosphine) Pd(0) (0.068 g, 0.059 mmol, 0.1 eq.), CuI (0.023 g, 0.118 mmol, 0.2 eq.) and DIPEA (0.153 g, 1.183 mmol, 0.21 ml, 2 eq). The mixture was stirred at room temperature for 15 h and further CuI (0.023 g, 0.118 mmol, 0.2 eq.) and triethylamine (5 ml) were added. The mixture was stirred at 80° C. for 8 h. The solvent was removed under high vacuum and the residue was purified by column chromatography (4% methanol in ethyl acetate) followed by preparative thin layer chromatography (4% methanol in ethyl acetate) to obtain the desired compound.

Off white solid: 0.024 g (10%)

¹H NMR (500 MHz, CDCl₃) δ 8.87 (1H, s, H4), 6.45 (1H, s, H5), 6.21 (1H, dd, J, 6.8, 2.0 Hz, H1'), 4.48 (2H, s, CH₂OCH₂CH₂), 4.34-4.29 (1H, m, H4'), 4.20-4.15 (1H, m, H5'a), 3.90-3.87 (1H, m, H5'b), 3.56 (2H, t, J, 6.65 Hz, OCH₂CH₂), 2.68-2.57 (1H, m, H2'a), 2.28-2.18 (1H, m, H2'b), 1.98-1.89 (2H, m, H3'), 1.67-1.58 (2H, qn, J, 6.9 Hz, OCH₂CH₂), 1.40-1.22 (20H, m, 10×CH₂), 0.90 (3H, t, J, 6.7 Hz, CH₃)

¹³C NMR (CDCl₃) δ 171.78 (C7a), 159.36 (C6), 154.75 (C2), 137.60 (C4), 107.62 (C4a), 102.36 (C5), 88.13 (C1'), 82.92 (C4'), 71.49 (OCH₂CH₂), 64.95 (CH₂OCH₂CH₂), 62.79 (C5'), 33.79 (C2'), 2×31.91 (double intensity), 29.65, 29.61, 2×29.58 (double intensity), 29.47, 29.35, 2×26.06 (double intensity), (10×CH₂), 23.74 (C3'), 22.68 (CH₂), 14.10 (CH₃).

MS (m/z): 449 (24%), [M+H]⁺, 471 (36%, [M+Na]⁺), 512 (100%, [M+MeCNNa]⁺), Accurate mass: C25H₄₁N₂O₅ requires 449.3015, Observed 449.3024

HPLC: H₂O/MeOH, 100%-0 (0-15 mins), 10-90% (15-20 mins), 10-90% (20-25 mins), 0-100% (25-35 mins), Rt: 24.87 mins, 86.39%.

3-(2',3'-dideoxy-ribo-β-L-furanosyl)-6-methyloxytridecylfuro[2,3-d]pyrimidin-2(3H)-one (Cf 3254)

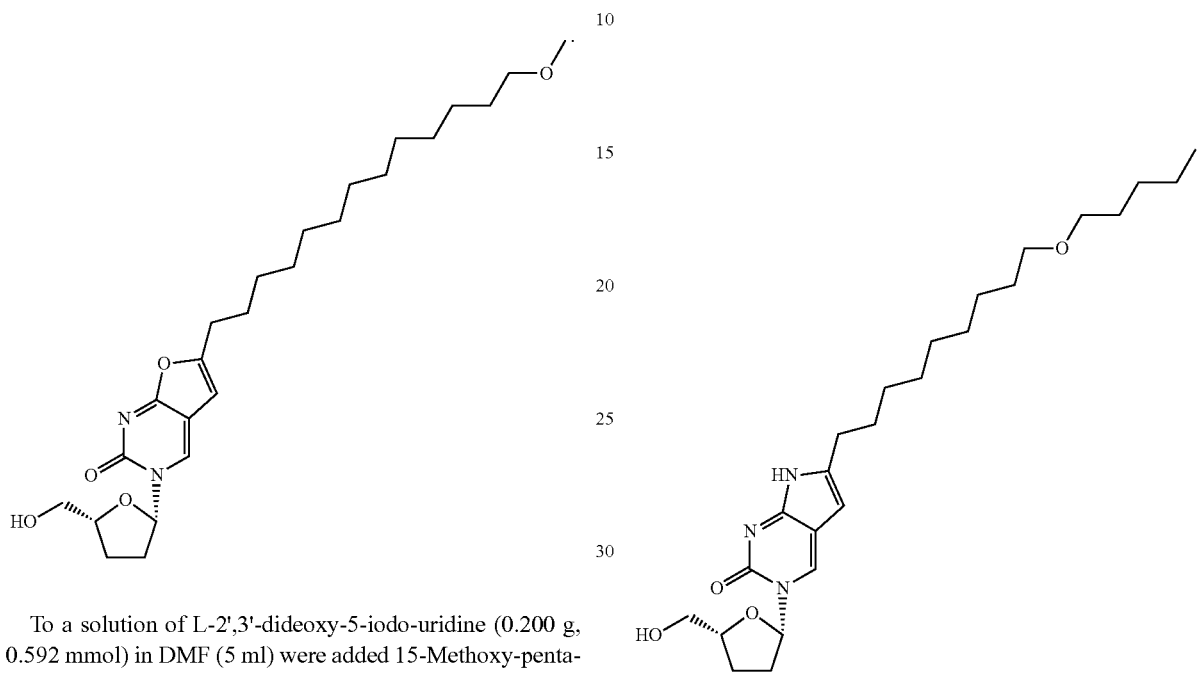

To a solution of L-2',3'-dideoxy-5-iodo-uridine (0.200 g, 0.592 mmol) in DMF (5 ml) were added 15-Methoxy-pentadec-1-yne (0.423 g, 1.774 mmol, 3.0 eq), tetrakis (triphenylphosphine) Pd(0) (0.068 g, 0.059 mmol, 0.1 eq.), CuI (0.023 g, 0.118 mmol, 0.2 eq.) and DIPEA (0.153 g, 1.183 mmol, 0.21 ml, 2 eq). The mixture was stirred at room temperature for 15 h and further CuI (0.023 g, 0.118 mmol, 0.2 eq.) and triethylamine (5 ml) were added. The mixture was stirred at 80° C. for 8 h. The solvent was removed under high vacuum and the residue was purified by column chromatography (3% methanol in ethyl acetate) to obtain the desired compound.

Off white solid: 0.050 g (19%)

¹H NMR (500 MHz, CDCl₃) δ 8.75 (1H, s, H4), 6.20 (1H, dd, J, 6.7, 2.4 Hz, H1'), 6.15 (1H, s, H5), 4.35-4.27 (1H, m, H4'), 4.19-4.13 (1H, m, H5'a), 3.88 (1H, dt, J, 12.0, 4.0 Hz, H5'b), 3.38 (2H, t, J, 6.7 Hz, CH₂CH₂O), 2.35 (3H, s, OCH₃), 2.84 (1H, J, 4.8 Hz, OH), 2.64 (2H, t̄, J, 7.5, αCH₂), 2.62-2.57 (1H, m, H2'a), 2.24-2.15 (1H, m, H2'b), 1.98-1.92 (1H, m, H3'), 1.71-1.65 (2H, m, βCH₂), 1.61-1.54 (2H, m, γCH₂), 1.40-1.23 (18H, m, 9×CH₂)

¹³C NMR (CDCl₃) δ 171.75 (C7a), 159.47 (C6), 155.02 (C2), 135.90 (C4), 107.22 (C4a), 99.08 (C5), 88.99 (C1'), 82.88 (C4'), 72.99 (OCH₂), 62.83 (C5'), 58.52 (OCH₃), 33.77 (C2'), 29.63, 29.56, 29.54, 2×29.48 (double intensity), 2×29.45 (double intensity), 29.23, 29.01, 28.25, 26.81, 26.12 (12×CH₂), 23.91 (C3').

MS (m/z): 449 (100%), [M+H]⁺, 471 (68%, [M+Na]⁺), 487 (84%, [M+K]⁺),

Accurate mass: C₂₅H₄₀N₂O₅ requires 449.3015, Observed 449.2997

HPLC: H₂O/MeOH, 100%-0 (0-15 mins), 10-90% (15-20 mins), 10-90% (20-25 mins), 0-100% (25-35 mins), Rt: 24.29 mins, 92.25%.

3-(2',3'-dideoxy-ribo-β-L-furanosyl)-6-pentyloxynonyl-pyrrolo[2,3-d]pyrimidin-2(3H)-one (Cf 3253)

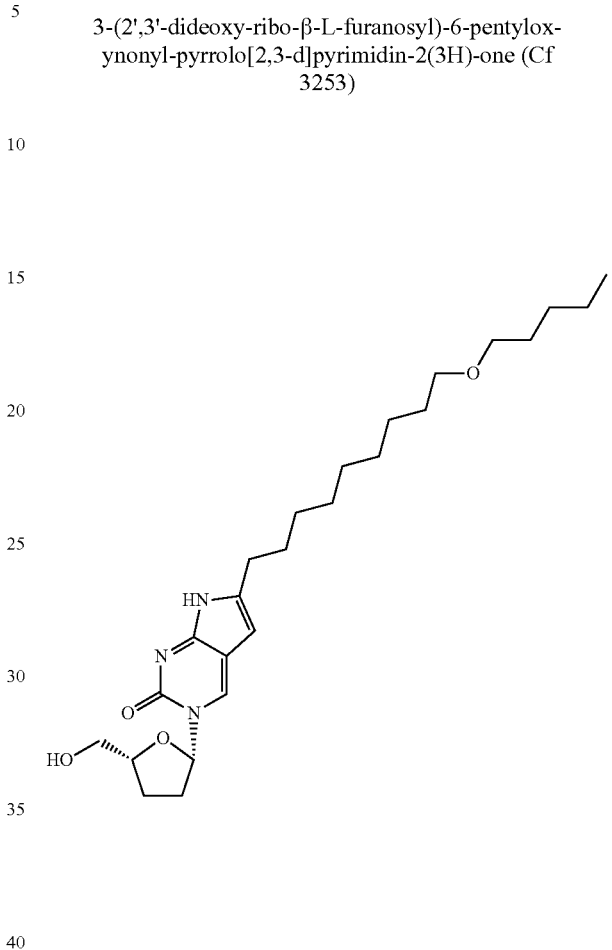

To a solution of L-3-(2',3'-dideoxy-ribosyl)-6-pentyloxynonylfuro[2,3-d]pyrimidin-2(3H)-one (Cf 3208) (0.050 g, 0.110 mmol) in methanol (5 ml), was added ammonia (30%, 5.00 ml) and the resulting solution was heated at 65° C. in a sealed tube for 72 hours. The solvent was removed under high vacuum and the residue obtained was purified by preparative tlc (10% methanol in dichloromethane) to obtain the desired compound.

White solid: 0.008 g (17%)

¹H NMR (500 MHz, CDCl₃) δ 10.63 (1H, bs, NH), 8.52 (1H, s, H4), 6.32-6.24 (1H, H1'), 5.89 (1H, s, H5), 4.34-4.26 (1H, m, H4'), 4.12-4.08 (1H, m, H5'a), 3.85 (1H, dd, J, 12.1, 3.9, Hz, H5'b), 3.45-3.31 (4H, m, CH₂OCH₂), 2.72-2.69 (2H, m, α-CH₂), 2.64-2.54 (1H, m, H2'a), 2.25-2.18 (1H, m, H2'b), 2.00-1.92 (2H, m, H3'), 1.74-1.65 (2H, m, β-CH₂), 1.50-1.04 (18H, m, 9×CH₂), 0.89 (3H, t, J, 6.8 Hz, CH₃)

¹³C NMR (CDCl₃) δ 159.02 (C7a), 154.91 (C2), 143.37 (C6), 134.39 (C4), 109.94 (C4a), 96.55 (C5), 88.79 (C1'), 82.43 (C4'), 71.07, 70.98 (CH₂OCH₂), 63.38 (C5'), 33.61 (C2'), 29.76, 29.45, 29.43, 29.42, 29.24, 28.99, 28.36, 28.08, 27.99, 26.15 (10×CH₂), 24.40 (C3'), 22.55 (CH₂), 14.04 (CH₃).

MS (m/z): 448 (66%), [M+H]⁺, 470 (100%, [M+Na]⁺),

Accurate mass: $C_{25}H_{42}N_3O_4$ requires 448.3175, Observed 448.3156

3-(2',3'-dideoxy-ribo-β-L-furanosyl)-6-pentyloxynonyl-N-methyl-pyrrolo[2,3-d]pyrimidin-2(3H)-one (Cf 3242)

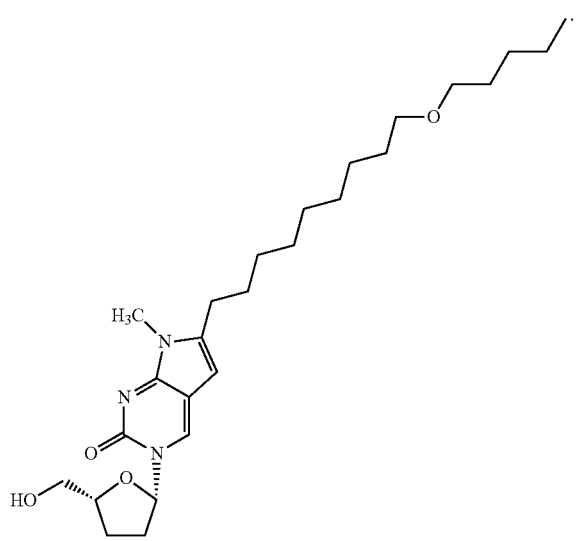 [SMILES: CCCCCOCCCCCCCCCc1cc2cn([C@@H]3CC[C@H](CO)O3)c(=O)nc2n1C]

To a solution of L-3-(2',3'-dideoxy-ribosyl)-6-pentyloxynonylfuro[2,3-d]pyrimidin-2(3H)-one (Cf 3208) (0.100 g, 0.223 mmol) in methanol (10 ml) was added aqueous methylamine (40% w, 3.00 ml) and the solution stirred at room temperature for 16 hours. The solvent was removed under high vacuum to obtain pale brown oil. This was dissolved in 1,4-dioxane (2 ml) and transferred into a round bottomed flask containing benzene (40 ml). was then added. The resulting mixture was heated under reflux using a Dean-Stark condenser in the presence of p-toluene sulphonyl chloride (2 mg) for 30 min. The solvent was removed in vacuo to afford brownish oil. This was purified by preparative tlc (10% MeOH in dichloromethane) to obtain the desired compound.

Off white solid: 0.040 g (39%)

$^1$H NMR (500 MHz, CDCl$_3$) δ 8.59 (1H, s, H4), 6.24 (1H, dd, J, 6.5, 2.5 Hz, H1'), 5.89 (1H, s, H5), 4.28-4.23 (1H, m, H4'), 4.09 (1H, dd, J, 11.9, 2.4 Hz, H5'a), 3.86 (1H, dd, J, 11.9, 2.5, Hz, H5'b), 3.56 (1H, bs, OH), 3.50 (1H, s, N-Me), 3.48 (4H, t, J, 6.7 Hz, CH$_2$OCH$_2$), 2.60-2.49 (3H, m, α-CH$_2$+ H2'a), 2.18-2.13 (1H, m, H2'b), 1.94-1.88 (2H, H3'), 1.69-1.63 (2H, m, β-CH$_2$), 1.59-1.57 (4H, m, 2×CH$_2$), 1.40-1.17 (16H, m, 8×CH$_2$), 0.89 (3H, t, J, 6.8 Hz, CH$_3$)

$^{13}$C NMR (CDCl$_3$) δ 158.16 (C7a), 155.10 (C2), 143.65 (C6), 134.60 (C4), 108.52 (C4a), 96.53 (C5), 88.75 (C1'), 82.66 (C4'), 70.96, 70.91 (CH$_2$OCH$_2$), 63.23 (C5'), 33.71 (C2'), 29.74, 2×29.40 (double intensity), 2×29.25 (double intensity), 29.17, 28.34 (7×CH$_2$), 27.71 (N—CH$_3$), 27.44 (β-CH$_2$), 26.78, 26.15 (2×CH$_2$), 24.38 (C3'), 22.51 (CH$_2$), 14.02 (CH$_3$).

MS (m/z): 462 (100%), [M+H]$^+$, 484 (76%, [M+Na]$^+$),

Accurate mass: $C_{26}H_{44}N_3O_4$ requires 462.3322, Observed 462.3336

Experimental Data:

Table I below sets out compounds embodying the present invention, having X and R$_1$ as in formula I above, and their activity with respect to vaccinia virus and measles virus.

Compound Cf2095 is a comparative example and does not embody the present invention.

Activity of compounds was tested using the three methods described below:
a. Vaccinia luciferase reporter assay (shown in Table I column 4)
b. Measles syncytium reduction assay (shown in Table I column 5)
c. Vaccinia plaque reduction assay (shown in Table I column 6)

a. Vaccinia Luciferase Reporter Assay

A recombinant vaccinia virus strain WR (VACV-WR) named 'v3' expressing the firefly luciferase gene was used to infect RK13 cells in the presence of indicated compounds at 10 uM and in the absence of compounds.

Recombinant vaccinia virus 'v3' was constructed using F13L deletion mutant vRB12 as recombinant VACV v240 (derived from donor plasmid p240) and expresses firefly luciferase (Clontech) under the control of the vaccinia virus early/late synthetic promoter (Davison, A. J. and Moss, B. 1993) from the F13L locus (Blasco, R. and Moss, B. (1991) Journal of Virology 65, 5910-5920). Virus stocks were grown up in Hela cells (ATCC CCL-2). RK13 cells (ATCC CCL-37) were grown in DMEM (Invitrogen-GIBCO), supplemented with 10% fetal bovine serum (Invitrogen-GIBCO; DMEMFC10), pretreated with compounds 30 minutes prior to infection with vaccinia virus at an moi of 0.2 in DMEM-FCO in triplicate 96 wells. The infected cells were collected 2 hrs post infection using PROMEGA Passive Lysis Buffer and expression of firefly luciferase was quantitated using a BMG labtech FLUOStar Optima luminometer. The raw data was acquired as relative light units and expressed in Table I as percent reduction of luciferase signal compared to cells infected in the absence of compounds.

b. Measles Syncytium Reduction Assay

Wildtype measles virus strain WTFb was used to infect B95a marmoset B lymphocytes (Sigma 01092505-1VL) in the presence of compounds at various concentrations and in the absence of compounds.

The measles wildtype strain WTFb uses the cd150 receptor expressed on B95a cells for virus entry. B95a cells are a subclone of the EBV transformed lymphoblastoid marmoset cell line B95-8 and were grown in DMEMFC10. Virus stocks were grown up in B95a cells. The infection with wildtype measles virus results after an incubation period of 2 to 3 days in syncytium formation, which can be easily observed using a phase contrast microscope. B95a cells in a 24 well plate, pretreated with compounds 30 minutes prior to infection, were infected with 50 syncytium forming units of mWTFb per well and monitored microscopically. Raw data was acquired observing the development of syncytia in the presence and absence of drug. The drug concentration resulting in a total suppression of syncytia formation is given in Table I as IC100.

c. Vaccinia Plaque Reduction Assay

VACV-WR was used to infect BSC-1 cells in the presence of compounds at various concentrations and in the absence of compounds.

VACV-WR virus stocks were grown up in Hela cells (ATCC CCL-2). BSC-1 monkey epithelial kidney cells (ATCC CCL-26) were grown in 24 well plates using DMEM (Invitrogen-GIBCO), supplemented with 10% fetal bovine serum (Invitrogen-GIBCO; DMEMFC10), pretreated with compounds 30 minutes prior to infection with 50 pfu per well of vaccinia virus in DMEMFCO overlaid with 1.2% Avicel microcrystalline cellulose (FMC). The infected cells were stained with crystal violet 3 days post infection, and plaque morphology was determined. Microscopical pictures of plaques were acquired and digitized, and plaque sizes measured. Activity was determined as reduced plaque size in 50% of observed plaques in a well and given in Table I as plaque size IC50 or 50% reduction of plaque numbers for HPMPC (Cidofovir; [(2S)-1-(4-amino-2-oxopyrimidin-1-yl)-3-hydroxypropan-2-yl]oxymethylphosphonic acid).

TABLE I

| Compound Cf | X | $R_1$ | VV % activity at 10 μM (a) | Measles IC 100/μM (b) | VV plaque size IC50 μM (c) |
|---|---|---|---|---|---|
| 3153 | O | n-Hexyl | 50 | | |
| 3174 | O | n-Heptyl | 41 | | |
| 3154 | O | n-Octyl | 23 | | |
| 3175 | O | n-Nonyl | 24 | 5-10 | |
| 3155 | O | n-Decyl | 24 | | |
| 3156 | O | n-Dodecyl | 65 | | |
| 3176 | O | p-butylphenyl | 44 | | |
| 3177 | O | p-pentylphenyl | 47 | | |
| 3210 | O | EtO—$C_9H_{18}$— | 72 | | |
| 3204 | O | PrO—$C_9H_{18}$— | 41 | | |
| 3207 | O | BuO—$C_9H_{18}$— | 29 | | |
| 3208 | O | PntO—$C_9H_{18}$— | 24 | 1-5 | 0.1 |
| 3209 | O | HexO—$C_9H_{18}$— | 46 | | |
| 3230 | O | HexO—$C_8H_{16}$— | 29 | | |
| 3231 | O | DecO—$C_4H_8$— | 26 | | |
| 3232 | O | TrisdecO—$CH_2$— | 45 | 1-5 | |
| 3254 | O | MeO—$C_{13}H_{26}$— | 59 | | |
| 3253 | NH | PntO—$C_9H_{18}$— | 52 | | |
| 3242 | NMe | PntO—$C_9H_{18}$— | 15 | 5-10 | |
| 2095* | O | PntO—$C_9H_{18}$— | 75 | Inactive | 1.5 |

*Compound Cf2095 is the -β-D- isomer of the compound Cf3208. Cf2095 is thus 3-(2',3'-dideoxy-ribo-β-D-furanosyl-6-pentyloxynonylfuro[2,3-d]pyrimidin-2(3H)-one. Cf2095 is a comparative compound and is included in Table I for convenience only. Although the chemical identity of X and $R_1$ for compound Cf2095 complies with Formula I above, the respective stereochemistry of the ribose C1 and C4 atoms for compound Cf2095 does not comply with Formula I above.

The data in Table I show that compounds embodying the present invention exhibit notable potency with respect to vaccinia virus and/or measles virus. Compounds Cf3154, Cf3175, Cf3155, Cf3208 and Cf3242, especially Cf3242, have greatly enhanced potency with respect to vaccinia virus, compared to comparative compound Cf2095. Compounds Cf3208 and Cf3232 have significant potency with respect to measles virus, in direct contrast to comparative compound Cf2095 which was inactive to measles virus.

The invention claimed is:

1. A compound having formula I:

I wherein
$R_1$ is selected from the group consisting of:
optionally substituted C5 to C20 alkyl;
substituted C1 to C20 alkyl, wherein a substituent on said C1 to C20 alkyl is selected from the group consisting of $R_2O$— and $R_2S$—, wherein $R_2$ is optionally substituted C1 to C15 alkyl; and
substituted aryl, wherein a substituent on said aryl is selected from the group consisting of optionally substituted C1 to C6 alkyl; and
X is selected from the group consisting of O, S, NH, NMe, NEt and NiPr;
or a pharmacologically acceptable salt thereof.

2. A compound according to claim 1, or a pharmacologically acceptable salt thereof, wherein $R_1$ is unsubstituted C6 to C12 alkyl.

3. A compound according to claim 1, or a pharmacologically acceptable salt thereof, wherein $R_1$ is an acyclic, saturated, unbranched and unsubstituted alkyl.

4. A compound according to claim 1, or a pharmacologically acceptable salt thereof, wherein $R_1$ is selected from the group consisting of n-hexyl-, n-heptyl-, n-octyl-, n-nonyl, n-decyl- and n-dodecyl-.

5. A compound according to claim 1, or a pharmacologically acceptable salt thereof, wherein $R_1$ is substituted C1 to C15 alkyl and $R_1$ comprises an unbranched, acyclic alkylene moiety having a single substituent, wherein that substituent is $R_2O$— present at the sole carbon atom of a C1 alkylene moiety or at a terminal position of said of a C2 to C15 alkylene moiety, wherein $R_2$ is acyclic, saturated, unbranched and unsubstituted and the total atomic backbone chain length of $R_1$ is from 12 to 16.

6. A compound according to claim 1 or 5 wherein $R_2$, or a pharmacologically acceptable salt thereof, is selected from the group consisting of Me-, Et-, Pr-, Bu-, Pnt-, Hex-, Non-, Dec- and Trisdec.

7. A compound according to claim 1, or a pharmacologically acceptable salt thereof, wherein $R_1$ is substituted phenyl.

8. A compound according to claim 7, or a pharmacologically acceptable salt thereof, wherein $R_1$ is para substituted phenyl.

9. A compound according to claim 1, 7 or 8, or a pharmacologically acceptable salt thereof, wherein $R_1$ is substituted aryl and the substituent on said aryl is unsubstituted C2 to C5 alkyl.

10. A compound according to claim 1, or a pharmacologically acceptable salt thereof, wherein X is O.

11. A compound according to claim 1, or a pharmacologically acceptable salt thereof, wherein X is NMe.

12. A compound selected from the group consisting of:
3-(2',3'-dideoxy-ribo-β-L-furanosyl)-6-hexylfuro[2,3-d]pyrimidin-2(3H)-one;
3-(2',3'-dideoxy-ribo-β-L-furanosyl)-6-septylfuro[2,3-d]pyrimidin-2(3H)-one;
3-(2',3'-dideoxy-ribo-β-L-furanosyl)-6-octylfuro[2,3-d]pyrimidin-2(3H)-one;
3-(2',3'-dideoxy-ribo-β-L-furanosyl)-6-nonylfuro[2,3-d]pyrimidin-2(3H)-one;
3-(2',3'-dideoxy-ribo-β-L-furanosyl)-6-decylfuro[2,3-d]pyrimidin-2(3H)-one;
3-(2',3'-dideoxy-ribo-β-L-furanosyl)-6-dodecylfuro[2,3-d]pyrimidin-2(3H)-one;
3-(2',3'-dideoxy-ribo-β-L-furanosyl)-6-(4-n-butylphenyl)[2,3-d]pyrimidin-2(3H)-one;
3-(2',3'-dideoxy-ribo-β-L-furanosyl)-6-(4-n-pentylphenyl)[2,3-d]pyrimidin-2(3H)-one;
3-(2',3'-dideoxy-ribo-β-L-furanosyl)-6-ethyloxynonylfuro[2,3-d]pyrimidin 2(3H)-one;
3-(2',3'-dideoxy-ribo-β-L-furanosyl)-6-propyloxynonylfuro[2,3-d]pyrimidin-2(3H)-one;

3-(2',3'-dideoxy-ribo-β-L-furanosyl)-6-butyloxynonyl-furo[2,3-d]pyrimidin-2(3H)-one;

3-(2',3'-dideoxy-ribo-β-L-furanosyl)-6-pentyloxynonyl-furo[2,3-d]pyrimidin-2(3H)-one;

3-(2',3'-dideoxy-ribo-β-L-furanosyl)-6-hexyloxynonyl-furo[2,3-d]pyrimidin-2(3H)-one;

3-(2',3'-dideoxy-ribo-β-L-furanosyl)-6-hexyloxyoctyl-furo[2,3-d]pyrimidin-2(3H)-one;

3-(2',3'-dideoxy-ribo-β-L-furanosyl)-6-decyloxybutyl-furo[2,3-d]pyrimidin-2(3H)-one;

3-(2',3'-dideoxy-ribo-β-L-furanosyl)-6-tridecyloxymethylfuro[2,3-d]pyrimidin-2(3H)-one;

3-(2',3'-dideoxy-ribo-β-L-furanosyl)-6-methyloxytridecylfuro[2,3-d]pyrimidin-2(3H)-one;

3-(2',3'-dideoxy-ribo-β-L-furanosyl-)-6-pentyloxynonyl-pyrrolo[2,3-d]pyrimidin-2(3H)-one; and 3-(2',3'-dideoxy-ribo-β-L-furanosyl)-6-pentyloxynonyl-N-methyl-pyrrolo[2,3-d]pyrimidin-2(3H)-one, or a pharmacologically acceptable salt thereof.

13. A method of treatment of a viral infection comprising administering to a patient in need thereof an effective dose of a compound according to claim 1, or a pharmacologically acceptable salt thereof.

14. A pharmaceutical composition comprising a compound according to claim 1, or a pharmacologically acceptable salt thereof, in combination with a pharmacologically acceptable excipient.

15. A method of preparing a pharmaceutical composition comprising the step of combining a compound according to claim 1, or a pharmacologically acceptable salt thereof, with a pharmaceutically acceptable excipient.

16. A method of preparing a compound according to claim 1, or a pharmacologically acceptable salt thereof, comprising reacting L-2',3'-dideoxy-5-halo-uridine with an alkyne of formula —C≡C—$R_1$ in the presence of a catalyst, wherein $R_1$ is as defined in claim 1 and uridine incorporates X as defined in claim 1.

17. A compound according to claim 1, or a pharmacologically acceptable salt thereof, wherein $R_1$ is unsubstituted C8 to C10 alkyl.

18. A compound according to claim 5, or a pharmacologically acceptable salt thereof, wherein the total atomic backbone chain length of $R_1$ is from 14 to 15.

19. The method of claim 13 wherein the viral infection is a vaccinia or a measles viral infection.

* * * * *